United States Patent
Mistretta

(10) Patent No.: US 8,825,138 B2
(45) Date of Patent: *Sep. 2, 2014

(54) METHOD FOR REDUCING MOTION ARTIFACTS IN HIGHLY CONSTRAINED MEDICAL IMAGES

(75) Inventor: Charles A. Mistretta, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 1100 days.

This patent is subject to a terminal disclaimer.

(21) Appl. No.: 12/208,412

(22) Filed: Sep. 11, 2008

(65) Prior Publication Data

US 2009/0076369 A1    Mar. 19, 2009

Related U.S. Application Data

(60) Provisional application No. 60/972,828, filed on Sep. 17, 2007, provisional application No. 61/023,454, filed on Jan. 25, 2008.

(51) Int. Cl.
| | |
|---|---|
| A61B 5/00 | (2006.01) |
| G01R 33/565 | (2006.01) |
| G06T 7/00 | (2006.01) |
| G01R 33/48 | (2006.01) |
| A61B 6/03 | (2006.01) |
| A61B 6/00 | (2006.01) |
| A61B 5/055 | (2006.01) |

(52) U.S. Cl.
CPC .......... *A61B 6/504* (2013.01); *G01R 33/56509* (2013.01); *A61B 5/7207* (2013.01); *A61B 6/03* (2013.01); *A61B 5/7285* (2013.01); *A61B 6/503* (2013.01); *A61B 6/482* (2013.01); *A61B 6/5288* (2013.01); *A61B 6/481* (2013.01); *A61B 6/527* (2013.01); *A61B 6/541* (2013.01); *G06T 7/00* (2013.01); *A61B 5/055* (2013.01); *G01R 33/4824* (2013.01)
USPC ........................... 600/427; 600/411; 382/128

(58) Field of Classification Search
USPC ......... 600/407, 410, 411, 420, 425, 426, 431; 382/128, 130, 131
See application file for complete search history.

(56) References Cited

U.S. PATENT DOCUMENTS 6,111,582 A * 8/2000 Jenkins .......................... 345/421
6,314,160 B1 11/2001 Kautz et al.

(Continued)

OTHER PUBLICATIONS

Wu et al; HYPR-TRICK: Highly Undersampled Hybrid Radial/Cartesian Acquisition with Highly Constrained Backprojection Reconstruction For Time Resolved MRI; Proc. Intl. Soc. Mag. Reson. Med. 14 (2006); 1 page.

(Continued)

*Primary Examiner* — Unsu Jung
*Assistant Examiner* — Amanda Lauritzen Moher
(74) *Attorney, Agent, or Firm* — Quarles & Brady, LLP

(57) ABSTRACT

A composite image is produced for use in HYPR processing a current image frame. The amount of a priori data used to form the composite is determined by the amount of subject motion. The current composite image may be spatially registered with the current image frame to offset subject motion before being used to form an updated composite image. Subject motion may be analyzed on a frame-by-frame basis, a region-by-region basis or a pixel-by-pixel basis to optimize the SNR of the updated composite image.

24 Claims, 22 Drawing Sheets

(56) References Cited

U.S. PATENT DOCUMENTS

| | | | |
|---|---|---|---|
| 7,358,730 | B2 | 4/2008 | Mistretta et al. |
| 7,408,347 | B2 | 8/2008 | Mistretta et al. |
| 7,519,412 | B2 * | 4/2009 | Mistretta ............... 600/407 |
| 7,545,901 | B2 | 6/2009 | Mistretta et al. |
| 7,647,088 | B2 | 1/2010 | Mistretta et al. |
| 7,711,166 | B2 | 5/2010 | Mistretta et al. |
| 7,865,227 | B2 * | 1/2011 | Mistretta ............... 600/413 |
| 7,917,189 | B2 * | 3/2011 | Mistretta ............... 600/410 |
| 7,991,452 | B2 * | 8/2011 | Mistretta et al. ......... 600/420 |
| 2007/0009080 | A1 | 1/2007 | Mistretta et al. |
| 2007/0010731 | A1 | 1/2007 | Mistretta et al. |
| 2007/0038073 | A1 | 2/2007 | Mistretta et al. |
| 2007/0106149 | A1 | 5/2007 | Mistretta et al. |
| 2007/0156044 | A1 | 7/2007 | Mistretta et al. |
| 2007/0156045 | A1 * | 7/2007 | Mistretta et al. ......... 600/410 |
| 2007/0167707 | A1 | 7/2007 | Mistretta et al. |
| 2007/0167728 | A1 | 7/2007 | Mistretta et al. |
| 2008/0199063 | A1 | 8/2008 | O'Halloran et al. |
| 2008/0219535 | A1 | 9/2008 | Mistretta et al. |
| 2009/0129651 | A1 | 5/2009 | Zagzebski et al. |
| 2009/0161932 | A1 * | 6/2009 | Chen ............... 382/131 |
| 2010/0286504 | A1 * | 11/2010 | Mistretta et al. ......... 600/420 |

OTHER PUBLICATIONS

Supanich et al; Dose Reduction in Neuro CT Exams Using Highly Constrained Back Projection (HYPR) Techniques; hppt://rsna2006.rsna.org; Nov. 30, 2006; 2 pages.

Mistretta, C.A.; Prospects for Acceleration and Dose Reduction in Selected MR and X-Ray CT Cardiovascular Applications; Proc. Intl. Soc. Mag. Reson. Med. 14 (2006); 1 page.

Mistretta et al; Highly Constrained Backprojection for Time-Resolved MRI; Mag. Reson. Med. 55:30-40 (2006).

Gert Schoonenberg, et al., "Adaptive spatial-temporal filtering applied to x-ray fluoroscopy angiography", Proceedings of SPIE vol. 5744 Medical Imaging 2005.

Tobias Schaeffter, et al., "Real-Time Adaptive Filtering for Projection Reconstruction MR Fluoroscopy", IEEE Transaction on Medical Imaging, vol. 22, No. 1, Jan. 2003.

K. V. Koladia, et al., "Rapid 3D PC-MRA Using Spiral Projection Imaging", Proc. Intl. Soc. Magn. Reson. Med. 13, 2005.

J. G. Pipe, et al., "Spiral Projection Imaging: a new fast 3D trajectory", Proc. Intl. Soc. Mag. Reson. Med. 13, 2005.

Jiang Hsieh, "Computed Tomography Principles, Design, Artifacts and Recent Advances", Chapter 3, SPIE Press 2003.

Wisconsin Alumni Research Foundation HYPE Portfolio Flow Chart; 3 pages; Jan. 19, 2011.

* cited by examiner

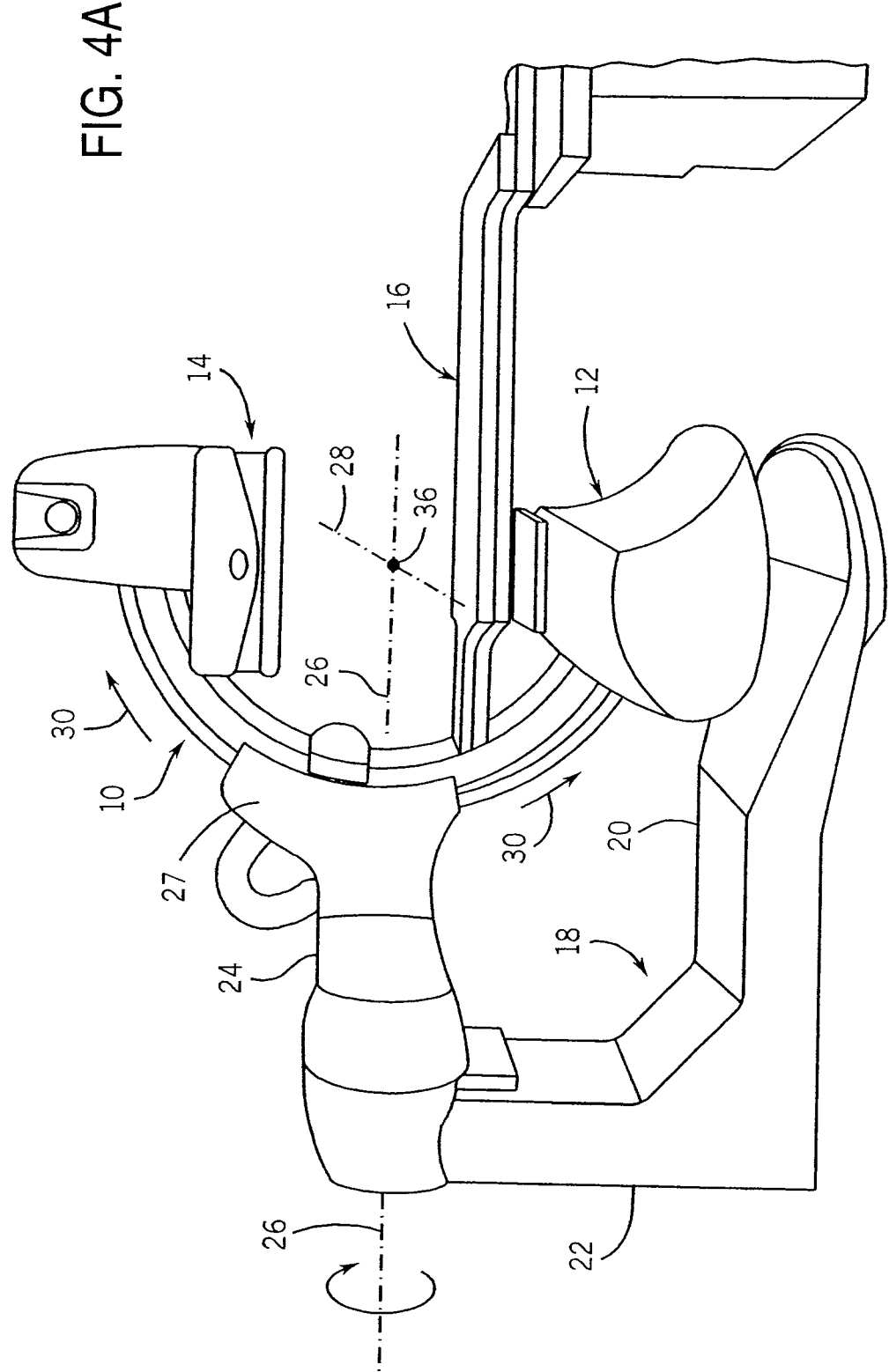

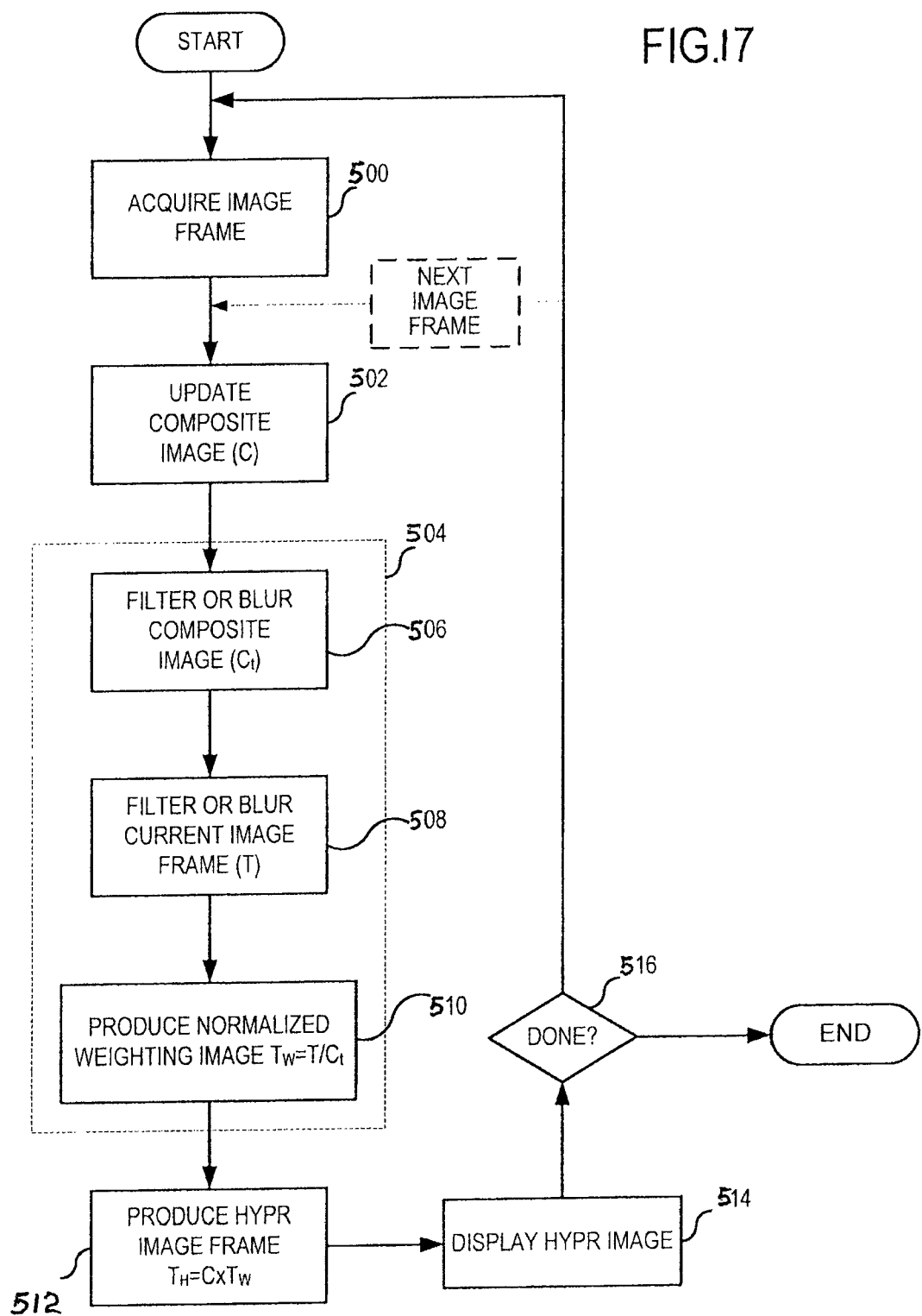

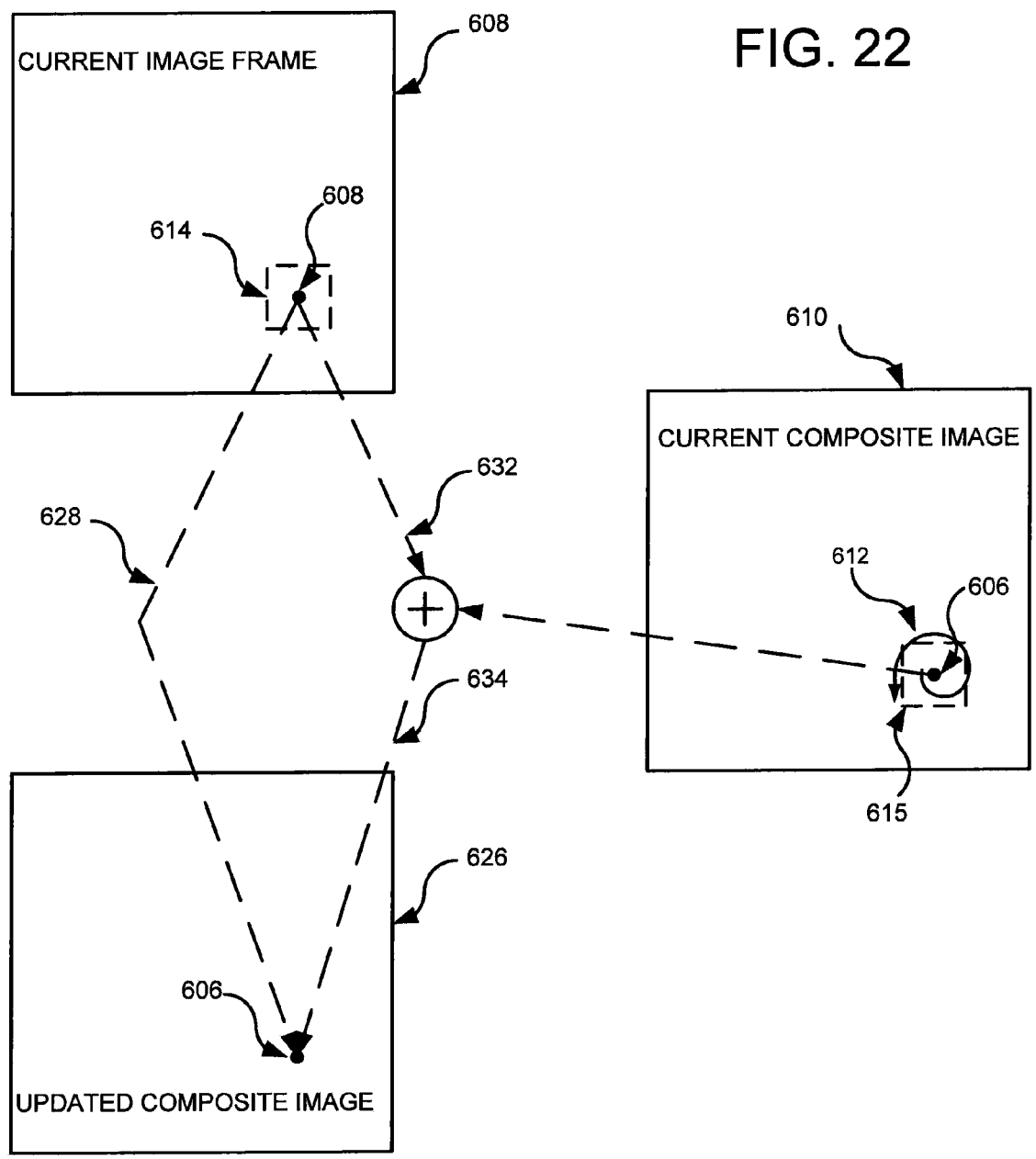

METHOD FOR REDUCING MOTION ARTIFACTS IN HIGHLY CONSTRAINED MEDICAL IMAGES

CROSS-REFERENCE TO RELATED APPLICATIONS

This application claims the benefit of U.S. Provisional patent application Ser. No. 60/972,828 filed on Sep. 17, 2007 and entitled "Method for Producing Highly Constrained X-Ray Radiograph Images" and U.S. Provisional patent application Ser. No. 61/023,454 filed on Jan. 25, 2008 and entitled "Method for Reducing Motion Artifacts in Highly Constrained Medical Images".

STATEMENT REGARDING FEDERALLY SPONSORED RESEARCH

This invention was made with government support under Grant Nos. NIH EB006393 and HL072260. The United States Government has certain rights in this invention.

This invention was made with government support under Grant No. EB006393 awarded by the National Institute of Health. The United States Government has certain rights in this invention.

BACKGROUND OF THE INVENTION

The field of the invention is medical imaging and particularly, methods for producing images using a highly constrained image reconstruction method.

Recently a new image reconstruction method known in the art as "HYPR" and described in co-pending U.S. patent application Ser. No. 11/482,372, filed on Jul. 7, 2006 and entitled "Highly Constrained Image Reconstruction Method" was disclosed and is incorporated by reference into this application. With the HYPR method a composite image is reconstructed from acquired data to provide a priori knowledge of the subject being imaged. This composite image is then used to highly constrain the image reconstruction process. HYPR may be used in a number of different imaging modalities including magnetic resonance imaging (MRI), x-ray computed tomography (CT), positron emission tomography (PET), single photon emission computed tomography (SPECT) digital tomosynthesis (DTS) and ultrasonic imaging.

As shown in FIG. 1, for example, when a series of time-resolved images 2 are acquired in a dynamic study, each image frame 2 may be reconstructed using a very limited set of acquired views. However, each such set of views is interleaved with the views acquired for other image frames 2, and after a number of image frames have been acquired, a sufficient number of different views are available to reconstruct a quality composite image 3 for use according to the HYPR method. A composite image 3 formed by using all the interleaved projections is thus a much higher quality image (i.e. high signal-to-noise ratio (SNR)), and this higher quality is conveyed to the image frame by using the highly constrained image reconstruction method 4.

A discovery of the HYPR method is that good quality images can be produced with far fewer projection signal profiles if a priori knowledge of the signal contour in the FOV 12 is used in the reconstruction process. Referring to FIG. 2, for example, the signal contour in the FOV 12 may be known to include structures such as blood vessels 18 and 20. That being the case, when the backprojection path 8 passes through these structures a more accurate distribution of the signal sample 14 in each pixel is achieved by weighting the distribution as a function of the known signal contour at that pixel location. As a result, a majority of the signal sample 14 will be distributed in the example of FIG. 2 at the backprojection pixels that intersect the structures 18 and 20. For a backprojection path 8 having N pixels this highly constrained backprojection may be expressed as follows:

$$S_n = (P \times C_n) \bigg/ \sum_{n=1}^{N} C_n \qquad (2)$$

where: $S_n$=the backprojected signal magnitude at a pixel n in an image frame being reconstructed;

P=the signal sample value in the projection profile being backprojected; and $C_n$=signal value of an a priori composite image at the $n^{th}$ pixel along the backprojection path. The composite image is reconstructed from data acquired during the scan, and may include that used to reconstruct the image frame as well as other acquired image data that depicts the structure in the field of view. The numerator in equation (2) weights each pixel using the corresponding signal value in the composite image and the denominator normalizes the value so that all backprojected signal samples reflect the projection sums for the image frame and are not multiplied by the sum of the composite image.

While the normalization can be performed on each pixel separately after the backprojection, in many clinical applications it is far easier to normalize the projection P before the backprojection. In this case, the projection P is normalized by dividing by the corresponding value $P_c$ in a projection through the composite image at the same view angle. The normalized projection $P/P_c$ is then backprojected and the resulting image is then multiplied by the composite image.

A 3D embodiment of the highly constrained backprojection is shown pictorially in FIG. 3 for a single 3D projection view characterized by the view angles θ and φ. This projection view is back projected along axis 16 and spread into a Radon plane 21 at a distance r along the back projection axis 16. Instead of a filtered back projection in which projection signal values are filtered and uniformly distributed into the successive Radon planes, along axis 16, the projection signal values are distributed in the Radon plane 21 using the information in the composite image. The composite image in the example of FIG. 3 contains vessels 18 and 20. The weighted signal contour value is deposited at image location x, y, z in the Radon plane 21 based on the intensity at the corresponding location x, y, z in the composite image. This is a simple multiplication of the backprojected signal profile value P by the corresponding composite image voxel value. This product is then normalized by dividing the product by the projection profile value from the corresponding image space projection profile formed from the composite image. The formula for the 3D reconstruction is $$I(x,y,z) = \Sigma(P(r,\theta,\phi) * C(x,y,z)_{(r,\theta,\phi)}/P_c(r,\theta,\phi) \qquad (2a)$$

where the sum (Σ) is over all projections in the image frame being reconstructed and the x, y, z values in a particular Radon plane are calculated using the projection profile value $P(r,\theta,\phi)$ at the appropriate $r,\theta,\phi$ value for that plane. $P_c(r,\theta,\phi)$ is the corresponding projection profile value from the composite image, and $C(x,y,z)_{r,\theta,\phi}$ is the composite image value at $(r,\theta,\phi)$.

The HYPR image reconstruction method has been used primarily to reduce image artifacts due to undersampling in MRI and x-ray CT. However, HYPR can also be used to improve the SNR of an image. For example, the image frames 2 may be acquired in a dynamic study in which the dosage (e.g., x-ray) or exposure time (e.g., PET or SPECT) is reduced for each image frame. In this case the composite image 3 is formed by accumulating or integrating measurements from the series of acquired low SNR image frames 2 to produce a higher SNR composite image 3. In this case, the highly constrained image 4 produced from each low SNR image frame 2 takes on the higher SNR of this composite image 3.

Another HYPR processing method is described in copending U.S. Patent application Ser. No. 60/901,728 filed on Feb. 19, 2007 and entitled "Localized and Highly Constrained Image Reconstruction Method", the teaching of which is incorporated herein by reference. With this localized HYPR method normalized weighting images are produced from each acquired image frame and each weighting image is multiplied by a high quality composite image which may be formed by accumulating or integrating acquired image frames. Each normalized weighting image is produced by blurring the acquired image frame with a filter and then dividing the blurred image frame with a similarly blurred version of the composite image. This localized HYPR method may be employed as the image reconstruction step where tomographic views of the subject are acquired, or it may be used to enhance the quality of radiograph images by imparting the low artifacts and high SNR qualities of the composite image to the radiograph image.

Regardless of which HYPR processing method is used, when the composite image is formed by integrating a window of acquired image frames, subject motion becomes an issue. If the window is set wide to integrate more image frames and thus produce a higher quality composite image, the composite image may be blurred due to subject motion. When there is substantial subject motion, therefore, the window must be narrowed to avoid blurring and this results in a lower quality composite image and hence lower quality HYPR-produced image frames.

SUMMARY OF THE INVENTION

The present invention is an improvement to the HYPR process in which a higher quality composite image may be produced when subject motion is present during the scan. More specifically, the composite image is produced by accumulating data from a series of acquired image frames and the number of image frames from which acquired data is accumulated is determined by the nature and the amount of detected subject motion.

A general object of the invention is to provide a HYPR processing method which adapts to produce the best image possible when subject motion occurs during the scan. This is accomplished by automatically varying the manner in which the current image frame is integrated to produce the current composite image as a function of detected subject motion. It is recognized that different regions in the field of view of the acquired image typically undergo different amounts of subject motion and that separate composite images may be adaptively integrated for each region. Thus, the quality of the composite image for each region may be maximized and used in the HYPR processing of the entire image. It is also recognized that subject motion may be determined on a pixel-by-pixel basis and the adaptive integration of each pixel with the composite image is accomplished based on the detected motion.

In one embodiment of the invention the composite image produced by integrating all the image frame data from a plurality of acquired image frames, and the number of image frames included is determined by detected subject motion. For example, an ECG signal can be monitored as each image frame is acquired of a subject's beating heart and from this the amount of cardiac motion can be implied. In portions of the cardiac cycle where motion is less, the composite image may be produced from a larger number of image frames than when cardiac motion is greater.

In another embodiment the composite image to be produced is divided into a set of small regions and the number of image frames integrated to form each composite image region is determined by the motion occurring only in each region. If no motion is occurring in a composite region, then the corresponding data from many image frames can be accumulated to form a very high quality regional composite image. On the other hand, if motion is detected in a region, the number of image frames that are integrated to form the corresponding regional composite image is substantially reduced to avoid the deleterious effects of subject motion. The regional composite images are then combined to form a single composite image that is used to perform the HYPR processing of each image frame. In the alternative, the composite regions may be separately HYPR processed with corresponding regions of an image frame and the resulting regional images combined into a single HYPR processed image frame.

In yet another embodiment of the invention the integration of acquired image frames into a composite image is determined on a pixel-by-pixel basis. In this embodiment the movement of the subject is determined for each pixel of the currently acquired image frame and the integration of the pixel value with the corresponding pixel value in other acquired image frames to produce the composite image is determined by the measured motion.

Another aspect of the invention is a method for updating a current composite image with data from the current image frame. If significant motion is detected between the current composite image and current image frame, data in the composite image is spatially registered with the current image frame before integrating the two. This registration and integration can be performed on a frame-by-frame basis, a region-by-region basis, or a pixel-by-pixel basis.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 4A and 4B are perspective views of an x-ray system which employs a preferred embodiment of the present invention;

FIG. 17 is a flow chart of the HYPR process employed in another embodiment of the invention;

FIG. 22 is a pictorial representation of the processing performed in the method of FIG. 21.

DETAILED DESCRIPTION OF THE PREFERRED EMBODIMENT

Figure 4B:
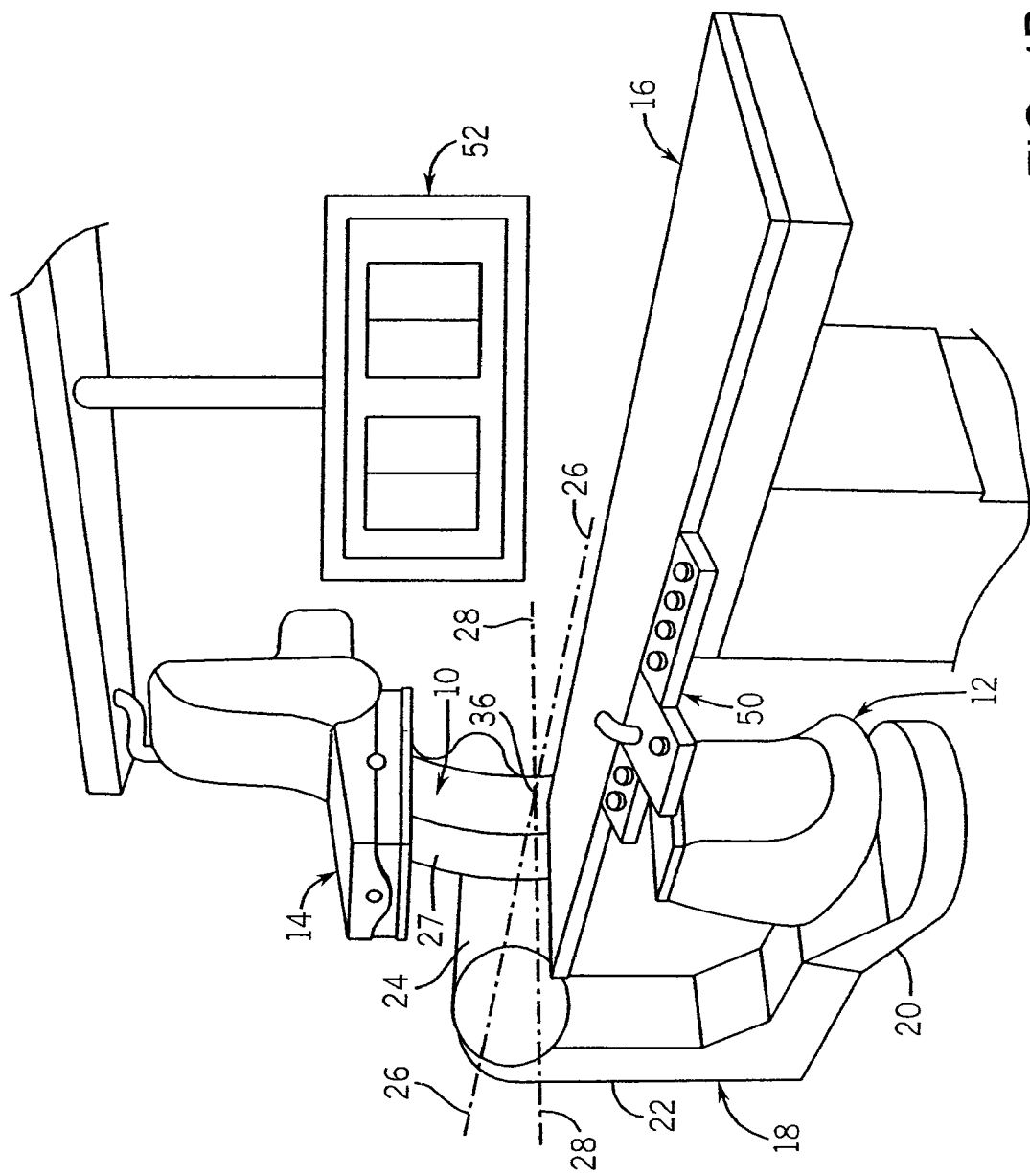
Figure 5:
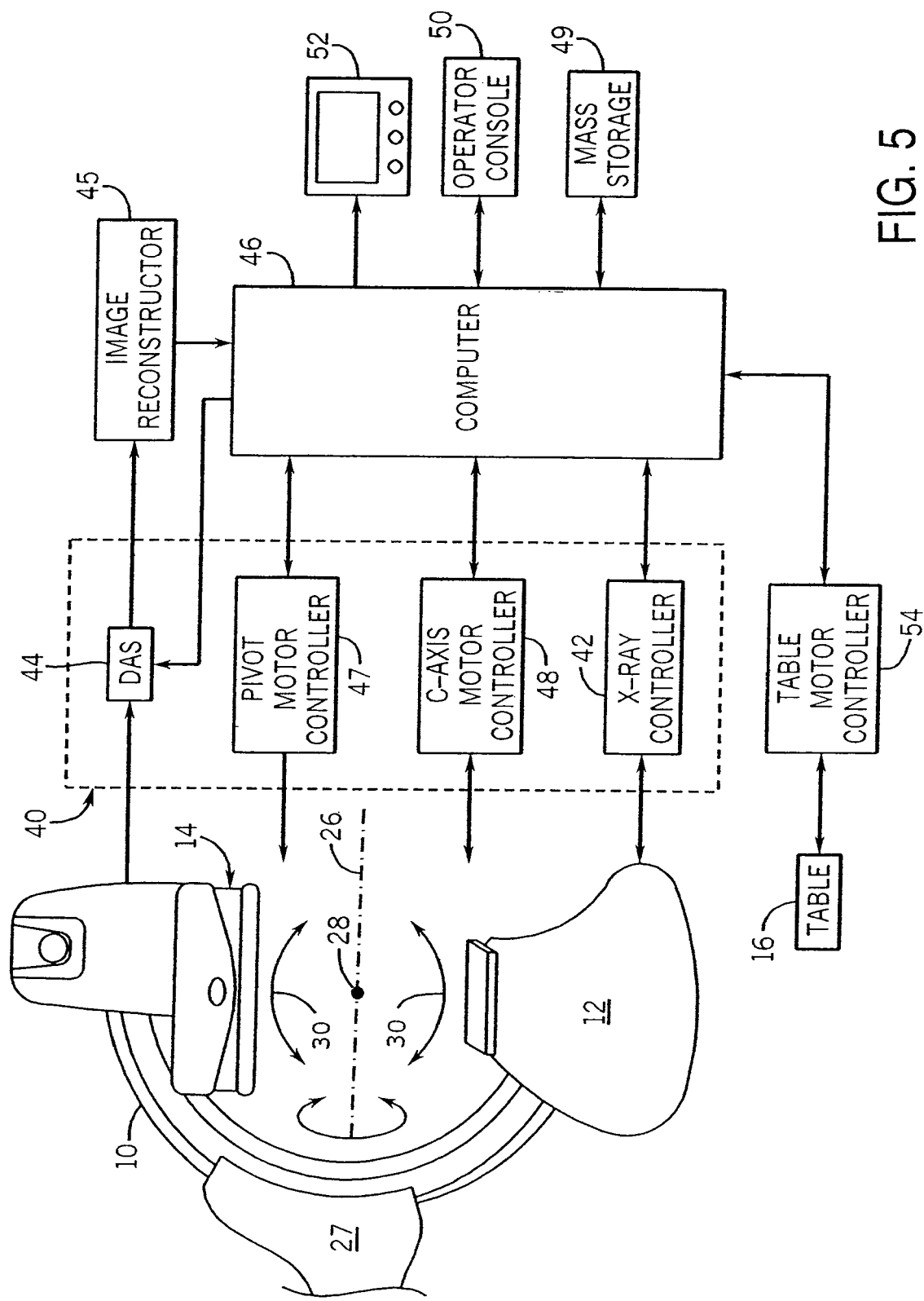
FIG. 5 is a schematic block diagram of the x-ray system of FIG. 4.
Figure 6:
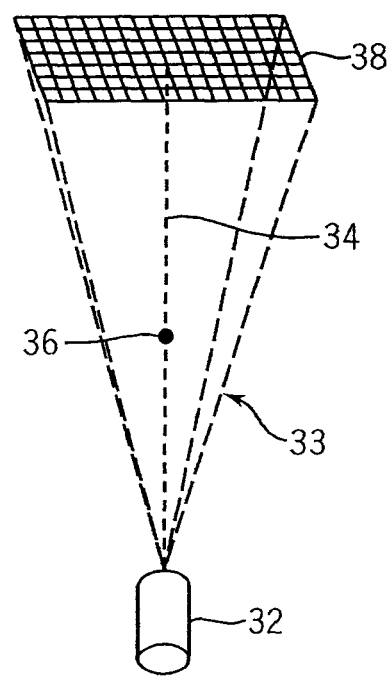
FIG. 6 is a pictorial view of an x-ray source and detector array which forms part of the x-ray system of FIG. 4.

Referring particularly to FIGS. 4 and 5, an x-ray system that may be used to acquire x-ray radiograph images for performing fluoroscopy and digital subtraction angiography is shown. It is characterized by a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient to perform a procedure.

The gantry includes an L-shaped pedestal 18 which has a horizontal leg 20 that extends beneath the table 16 and a vertical leg 22 that extends upward at the end of the horizontal leg 20 that is spaced from of the table 16. A support arm 24 is rotatably fastened to the upper end of vertical leg 22 for rotation about a horizontal pivot axis 26. The pivot axis 26 is aligned with the centerline of the table 16 and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other at an isocenter 36 located above the table 16 and they are perpendicular to each other.

The x-ray source assembly 12 is mounted to one end of the C-arm 10 and the detector array assembly 14 is mounted to its other end. As will be discussed in more detail below, the x-ray source 12 emits a cone beam of x-rays which are directed at the detector array 14. Both assemblies 12 and 14 extend radially inward to the pivot axis 26 such that the center ray of this cone beam passes through the system isocenter 36. The center ray of the cone beam can thus be rotated about the system isocenter around either the pivot axis 26 or the C-axis 28, or both during the acquisition of x-ray attenuation data from a subject placed on the table 16.

As shown in FIG. 5, the x-ray source assembly 12 contains an x-ray source 32 which emits a cone beam 33 of x-rays when energized. The center ray 34 passes through the system isocenter 36 and impinges on a two-dimensional flat panel digital detector 38 housed in the detector assembly 14. The detector 38 is a 2048 by 2048 element two-dimensional array of detector elements having a size of 41 cm by 41 cm. Each element produces an electrical signal that represents the intensity of an impinging x-ray and hence the attenuation of the x-ray as it passes through the patient. The detector array is able to acquire up to 30 radiograph frames per second to depict the procedure being performed in real time.

Referring particularly to FIG. 5, the orientation of the assemblies 12 and 14 and the operation of the x-ray source 32 are governed by a control mechanism 40 of the CT system. The control mechanism 40 includes an x-ray controller 42 that provides power and timing signals to the x-ray source 32. A data acquisition system (DAS) 44 in the control mechanism 40 samples data from detector elements 38 in some modes of operation and passes the data to an image reconstructor 45. The image reconstructor 45, receives digitized x-ray data from the DAS 44 and performs high speed image reconstruction in some modes of system operation. When operated in the radiograph mode, however, the data is passed directly through as a radiograph image frame. The 2D radiograph image is applied as an input to a computer 46 which performs the highly constrained image processing according to the present invention, stores the image in a mass storage device 49 and displays the image on a 2D display 52.

The control mechanism 40 also includes pivot motor controller 47 and a C-axis motor controller 48. In response to motion commands from the computer 46 the motor controllers 47 and 48 provide power to motors in the x-ray system that produce the rotations about respective pivot axis 26 and C-axis 28. These motion commands are produced in response to manual input from the attending physician.

The computer 46 also receives commands and scanning parameters from an operator via console 50 that has a keyboard and other manually operable controls. The associated display 52 allows the operator to observe the image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

The above described x-ray system may be operated in a fluoroscopic mode to produce two-dimensional images in real time. Typically, this mode is used when a procedure such as catherization is performed on the patient and the fluoroscopic images are used to help guide the procedure. The requirements are image frames produced with an SNR sufficient to see the instrument being guided and the surrounding anatomy, with a frame rate sufficient to provide near realtime images of the procedure, and with an x-ray dose as low as possible. The HYPR highly constrained image processing procedure described in pending U.S. patent application Ser. No. 11/482,372 filed on Jul. 7, 2006 and Ser. No. 12/032,240 filed on Feb. 15, 2007 enables the x-ray dose needed to acquire each 2D radiograph image frame to be significantly reduced without significantly affecting the other two requirements. This dose reduction is implemented by reducing the x-ray tube current. For example, the x-ray tube current may be reduced from 10 ma to 1 ma without any significant reduction in image quality. To employ the HYPR process a composite image must be produced by combining, or integrating the data from a plurality of acquired image frames. The larger the number of combined image frames, the higher the SNR of the composite image and the higher the SNR of the HYPR processed image frame. However, because there is typically subject motion during the acquisition of the series of fluoroscopic images, the composite image can become blurred if this motion is not taken into consideration.

In the first embodiment of the invention subject motion is measured on a frame-by-frame basis. The number of image frames combined to form the composite image is determined by measuring subject motion in the current image frame. When little motion is detected, the composite image is formed by combining a larger number of other acquired image frames with the current image frame.

Figure 1:
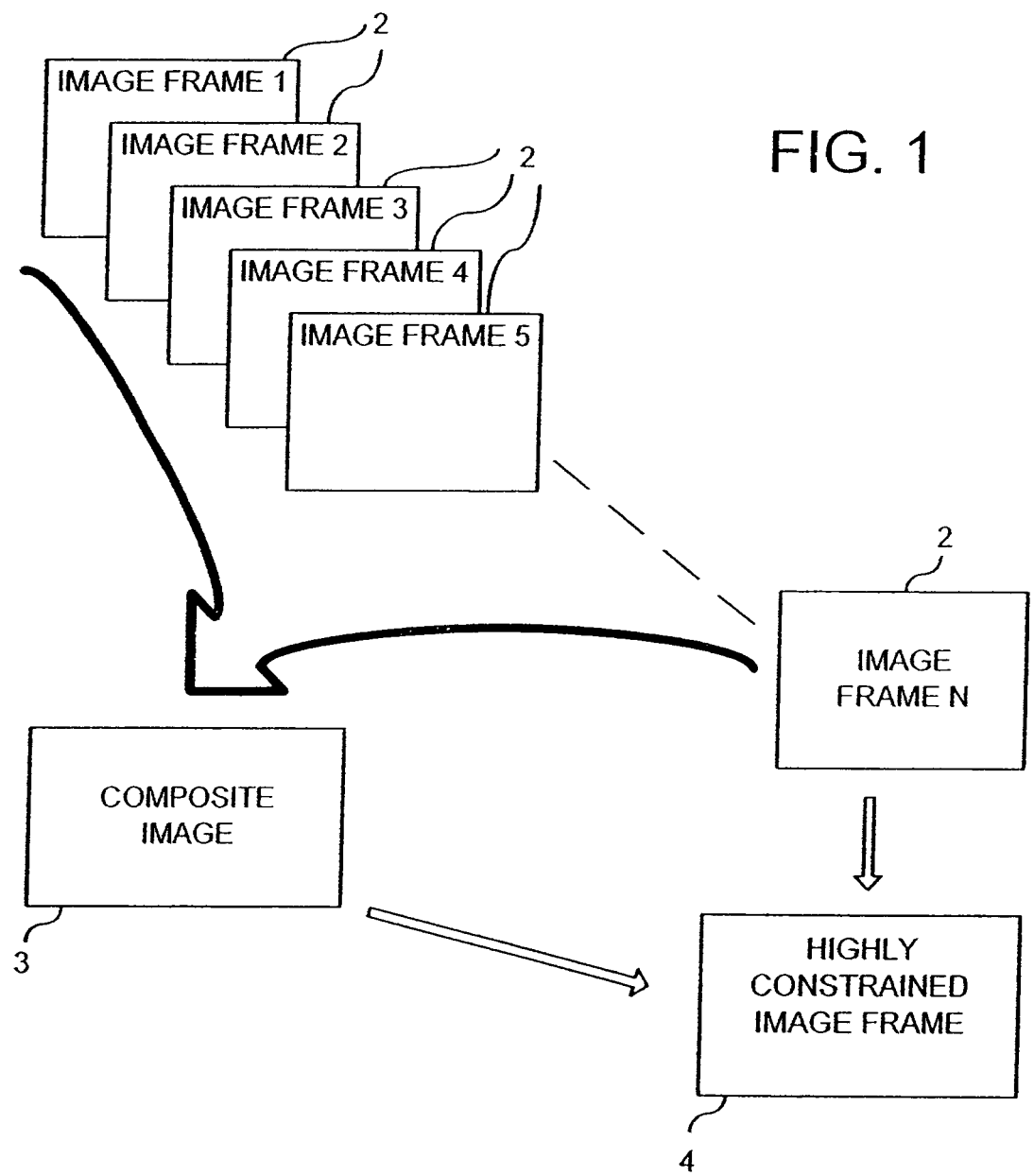
FIG. 1 is a pictorial view illustrating the application of the present invention to medical imaging applications.
Figure 2:
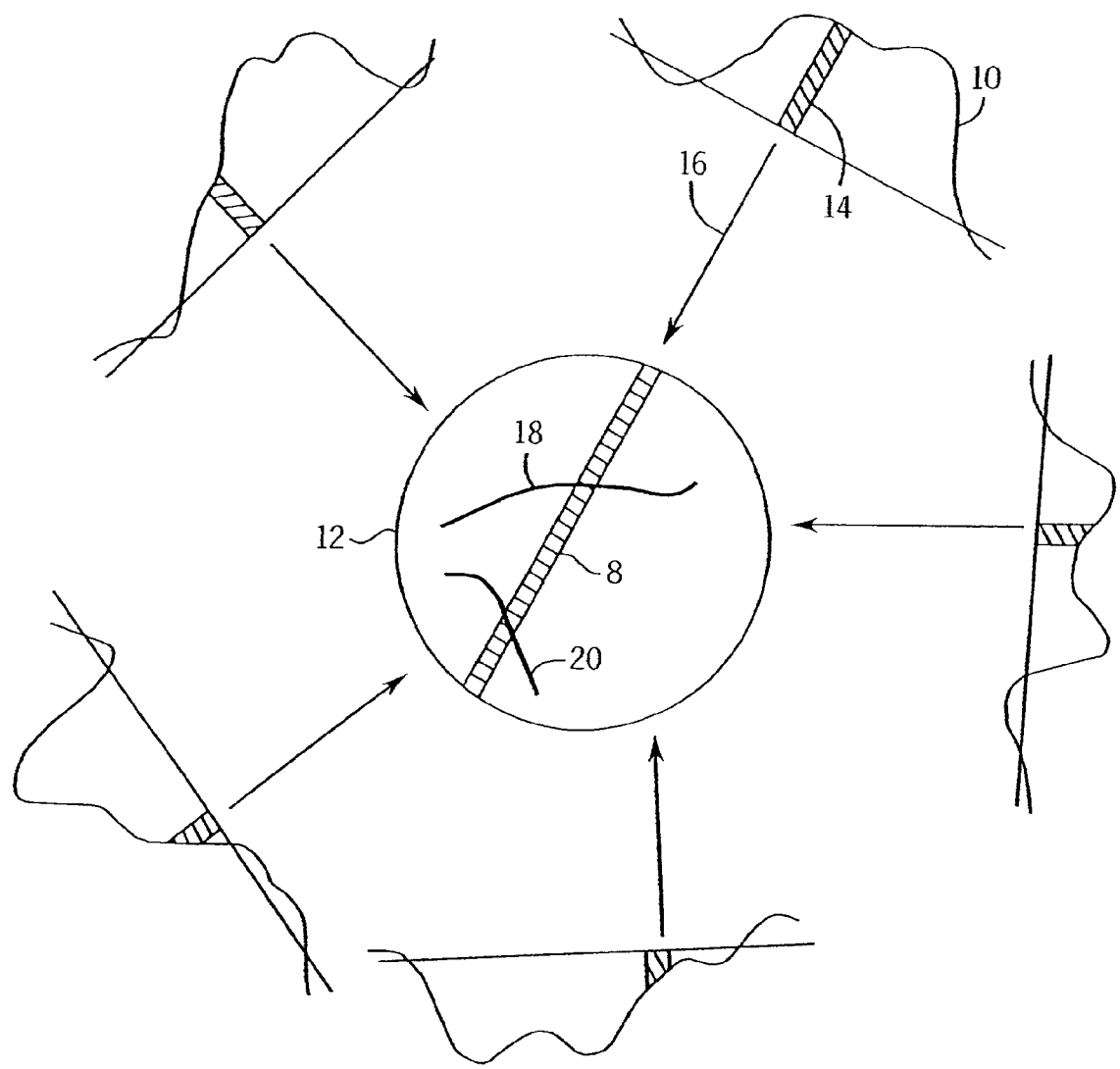
FIG. 2 is a pictorial representation of a highly constrained 2D backprojection method.
Figure 3:
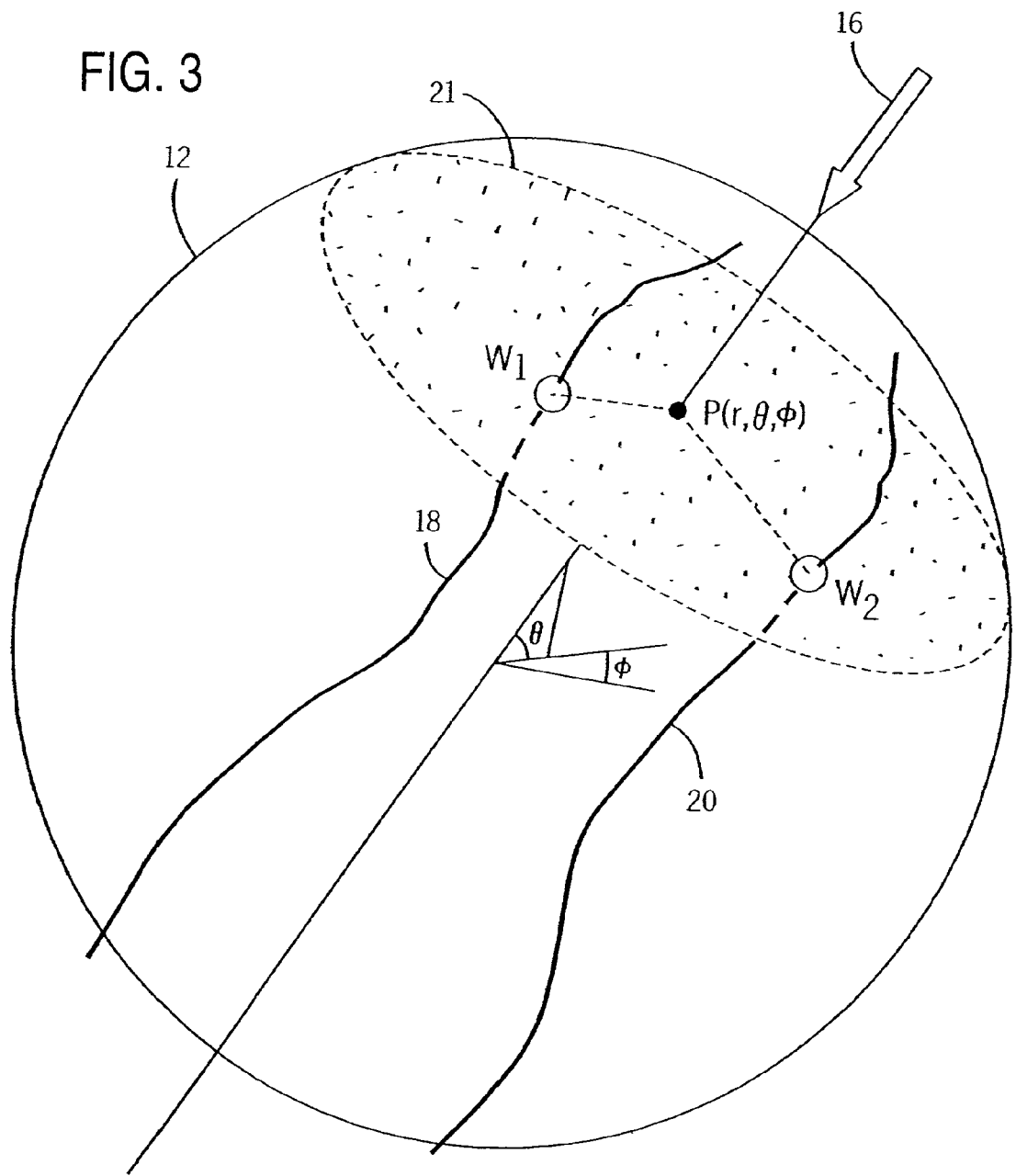
FIG. 3 is a pictorial representation of a highly constrained 3D backprojection method.

Referring particularly to FIGS. 1 and 17, the highly constrained image processing is carried out by a program executed by the computer 46 on acquired 2D radiograph image frames 2. As each image frame 2 is acquired as indicated at process block 500, it is stored and a copy is used to update a composite image 3 as indicated at process block 502. The composite image 3 is an accumulation of the current radiograph image frame 2 with a preselected number of other acquired radiograph image frames 2. The accumulation step is the matrix addition of corresponding pixels in the 2D image frames 2 divided by the number of image frames contributing to the accumulation. The result is a composite image 3 that has an increased SNR that is directly proportional to the square root of the preselected number of accumulated image frames 2. For example, if 36 2D image frames 2 are accumulated, the SNR will be 6 times the SNR of a single 2D image frame 2. As will be discussed further below, the number of image frames 2 used to form the composite image will depend on the particular clinical procedure being performed.

As indicated generally at 504, the next step is to produce a normalized weighting image using the current 2D radiograph image frame 2 and the updated composite image 3. There are a number of different ways to perform this step and the preferred method is shown in FIG. 17. More specifically, the updated composite image 3 is "blurred" by filtering as indicated at process block 506. More specifically, the filtering is a convolution process in which the updated 2D composite image array 3 is convolved with a filter kernel. In the preferred embodiment the filter kernel is a 7×7 square filter kernel. The kernel size should be selected so that when the blurring is done the kernel does not include much information from outside the subject of interest (for example a blood vessel). The filter kernel should be on the order of the dimension of the objects being examined or somewhat smaller. Gaussian or other smooth filter kernels may also be used and the resulting filter function being performed is essentially low pass filtering.

Referring still to FIG. 17, the current 2D image frame 2 is also blurred or filtered in the same manner as indicated at process block 508. That is, the current 2D radiograph image frame array 2 is convolved with the filter kernel to perform a low pass filtering function. As indicated at process block 510, the normalized weighting image ($T_W$) is then produced by dividing pixel values in the filtered current image frame (T) by the corresponding pixel values in the filtered composite image ($C_t$).

As indicated at process block 512, a highly constrained (HYPR) image frame 4 is then produced. This image frame 4 is produced by multiplying the updated composite image array 3 by the normalized weighting image array ($T_W$). This is a multiplication of corresponding pixel values in the two images. The resulting 2D HYPR image 4 is then output to the display 52 as indicated at process block 514 and the system loops back to acquire and process the next 2D radiograph image frame 2. When the procedure is completed, as determined at decision block 116, the program ends.

Figure 18:
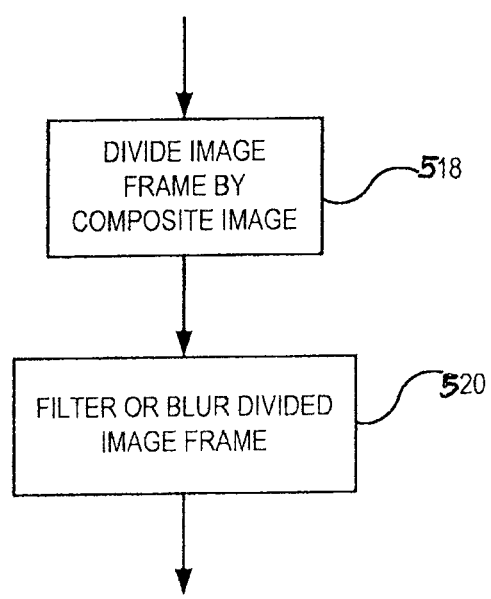
FIG. 18 is a flow chart of an alternative method used in the process of FIG. 17.
Figure 19:
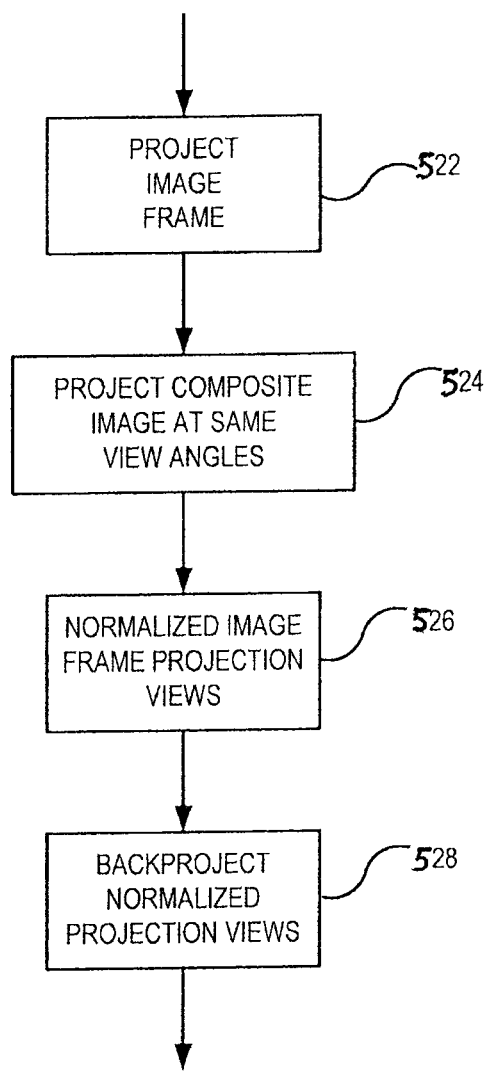
FIG. 19 is a flow chart of yet another alternative method used in the process of FIG. 17.

As indicated above, there are a number of alternative methods for producing the normalized weighting image ($W_T$). Two of these methods are illustrated in FIGS. 18 and 19. Referring particularly to FIG. 18, the first alternative method includes a first step indicated at process block 518 of dividing the acquired 2D radiograph image frame array 2 by the updated composite image (C) 3. This is a division of every pixel value in the acquired image frame array 2 by the corresponding pixel value in the updated composite image array 3. The resulting 2D divided image frame is then blurred or filtered as indicated at process block 120 to produce the normalized weighting image ($T_W$). This filtering operation is the same convolution process discussed above with respect to process blocks 506 and 508.

Another alternative method for producing the normalized weighting image ($T_W$) is illustrated in FIG. 19. This method transforms the acquired 2D radiograph image frame 2 to Radon space by taking projection views of the image from different view angles as indicated at process block 522. As indicated at process block 124, the updated composite image 3 is also transformed to Radon space by calculating projection views at the same set of view angles used to transform the 2D radiograph image frame 2. As indicated at process block 526 the image frame projection views P are then normalized by dividing them by the composite image projection views $P_C$. This is a division of corresponding elements in the projections P and $P_C$ at the same view angle. The normalized weighting image ($T_W$) is then produced at process block 128 by back projecting the normalized projections (P/$P_C$) in a conventional manner. This is not a filtered backprojection, but a straight forward backprojection.

As indicated above, the number of radiograph image frames 2 that are accumulated to form the composite image 3 will depend on the clinical application. Where there is rapid motion in the field of view of the acquired radiograph image frames, fewer should be accumulated so that the rapidly moving structure is not blurred. On the other hand, when a clear image with little noise is required the number of accumulated radiograph image frames 2 should be increased. In other words, the amount of subject motion is determined from the particular clinical application and this determines the size of the time window over which prior data may be accumulated.

There are also clinical applications where the number of accumulated image frames may be dynamically changed during the procedure. For example an ECG signal that indicates cardiac phase may be used to change the number of accumulated image frames. During diastole as determined from the ECG signal there is little cardiac motion and more image frames may be accumulated for the composite image 3 than during systole when there is more cardiac motion. For example, 3 image frames may be accumulated during systole and 6 to 10 image frames may be accumulated during diastole.

Not only is there a choice in the number of radiograph image frames 2 that are accumulated to form the updated composite image 3, but the location of the current image frame in a time window defined by the accumulated image frames can also be selected. One choice, of course, is to place the current image frame 2 at the end of the time window. In other words, all of the other included image frames 2 are acquired before the current image frame 2. However, because of the high frame rate used in x-ray fluoroscopy it is also advantageous to include image frames acquired in a time window that extends both before and after the current image frame 2. This will impose a small time delay that detracts from the real time nature of fluoroscopy, but in many medical procedures this is inconsequential.

It can be demonstrated that the SNR of each HYPR image frame 4 is dominated by the SNR of the composite image 3. SNR is calculated as the ratio of object signal level to the noise standard deviation within the object and CNR is calculated as the difference between the object and background signal levels divided by the standard deviation of the background noise.

Given the noise reduction achieved with the composite image, it is possible to perform fluoroscopy at reduced beam current (mA), and lower dose, without loss of SNR. Composite image SNR is theoretically proportional to SNR $\propto \sqrt{N \cdot mA}$, where N=number of frames per composite. Thus mA can theoretically be reduced by a factor of the square root of N. The number of frames N in the composite is constrained by object motion. Undesirably high N can result in reduction of catheter tip visibility due to motion blur. The goal is to realize maximum dose reduction while ensuring suitable catheter visibility.

It should be apparent to those skilled in the art that the above HYPR processing can also be performed on fluoroscopic image frames acquired at dual energies. In such a clinical application the two acquired fluoroscopic images would be combined first in the usual manner and the resulting image frame processed as described above. For example, the two different energy images may be combined to eliminate bone from the fluoroscopic image that is HYPR processed.

Figure 20:
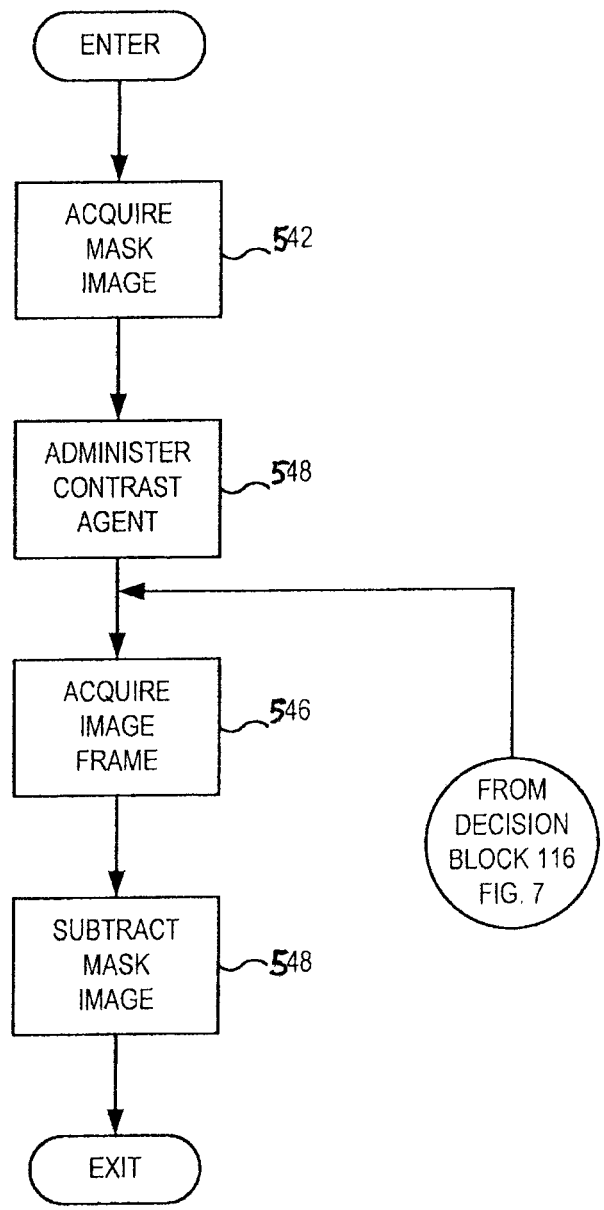
FIG. 20 is a flow chart of a modified version of the process of FIG. 17.

The present invention may also be used in a digital subtraction angiography (DSA) dynamic study in which a series of image frames are acquired as a contrast agent flows into vasculature of interest. The acquisition of the image frames is done as part of a procedure in which a contrast agent such as iodine is administered to the patient to enhance blood brightness in the radiograph. In this case the image frame acquisition 500 is more complex as indicated in FIG. 20. As indicated at process block 542, a pre-contrast "MASK" image is acquired first. This MASK image should have good SNR and it is acquired at full x-ray dose (e.g., 10 ma x-ray tube current). The contrast agent is then administered as indicated at process block 544 and the contrast flows through the patient's vasculature to the region of interest.

A low-dose image frame is acquired as indicated at process block 546 and the MASK image is subtracted from it as indicated at process block 548. The image frame may be acquired at a lower dose level (e.g., 1 ma x-ray tube current) and the tissues surrounding the contrast enhanced blood is subtracted therefrom to provide a "sparse" image which is very good for the HYPR processing that follows as described above. In this embodiment each DSA image frame is HYPR processed and displayed in near real time as the dynamic study progresses. The system loops back to process block 546 to acquire the next DSA image frame.

As with the fluoroscopic embodiment it should be apparent that the DSA procedure can also be performed at dual energies. In such case the MASK image is formed from two images acquired at different energy levels and each image frame acquired at process block 546 is also acquired at the same two energy levels and combined in the same manner to remove selected tissues.

The above-described HYPR processing is performed in near real time on single image frames acquired as indicated at process block 500. However, the same HYPR processing can also be used in clinical applications where a series of image frames are acquired at process block 500 before the HYPR processing of each image frame is performed. In such applications the HYPR processing loops back to process block 540 to process the next previously acquired image frame, rather than acquiring another image frame as described above.

Whereas the number of image frames that are combined to form the composite image in this first embodiment of the invention adapts to the amount of subject motion in the image frame field of view, in the embodiments now to be described the image frame field of view (FOV) is divided into regions and subject motion is measured in each region. The number of image frames combined to form the composite image is then determined on a region-by-region basis such that the composite image regions with little motion are formed by combining many acquired image frames and composite image regions with more motion are formed by combining fewer acquired image frames.

Figure 7:
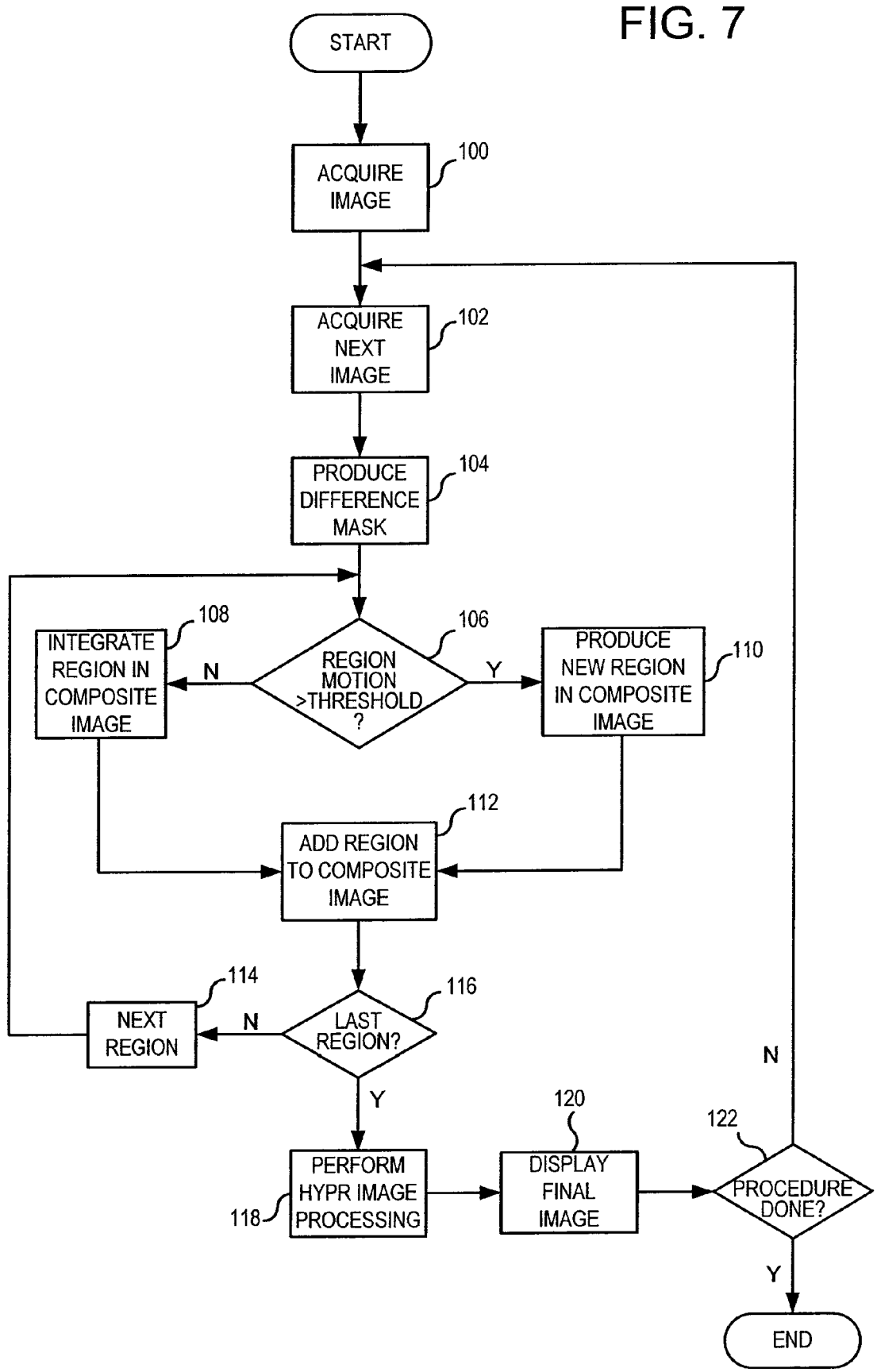
FIG. 7 is a flow chart which describes the steps used to HYPR process image frames acquired with the x-ray system of FIG. 4.
Figure 9:
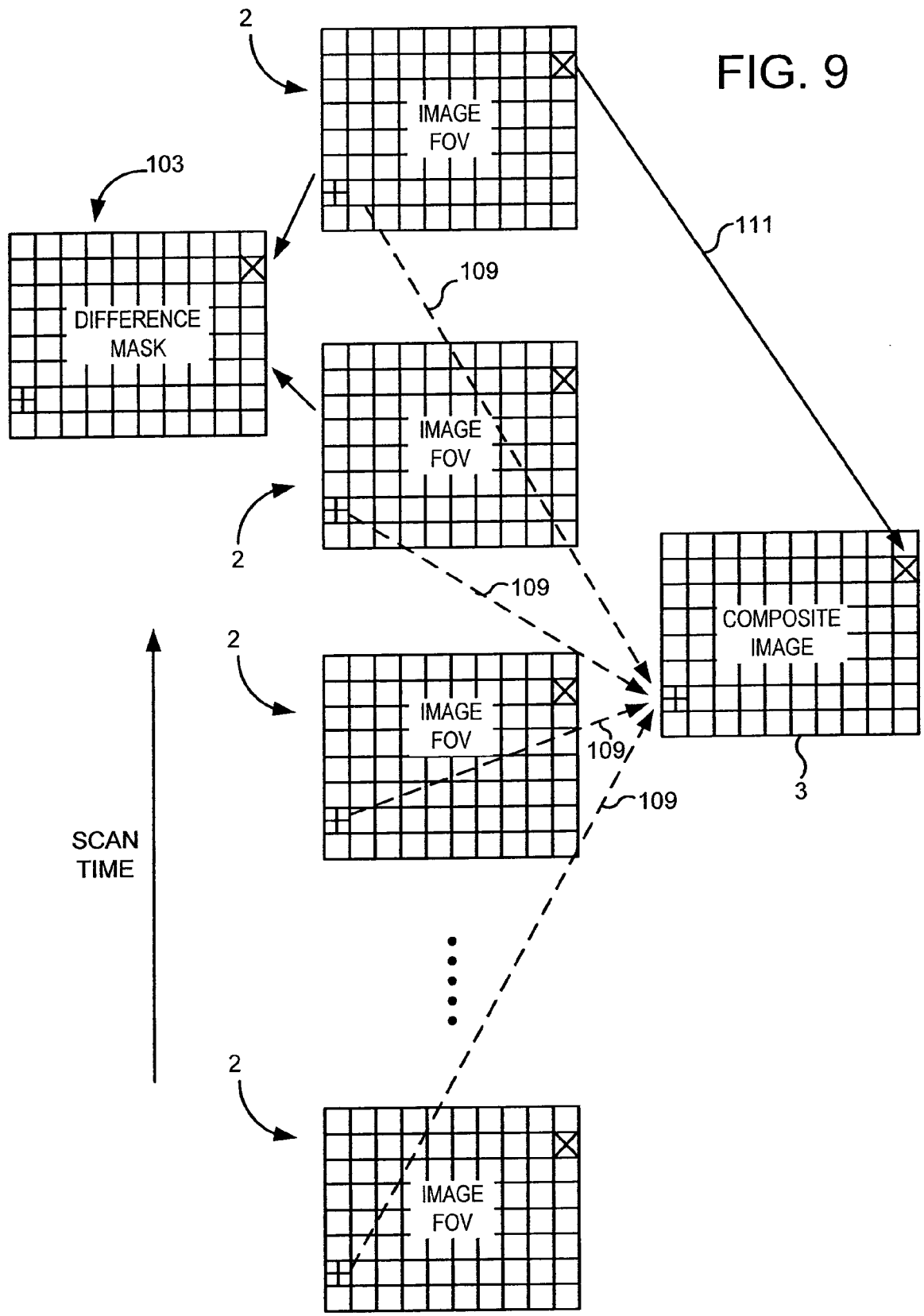
FIG. 9 is a schematic depiction of how a composite image is formed in the method of FIG. 7.

Referring particularly to FIGS. 1 and 7, the highly constrained image processing is carried out by a program executed by the computer 46 on acquired 2D radiograph image frames 2. As successive image frames 2 are acquired as indicated at process blocks 100 and 102, they are stored and used to produce a difference mask as indicated at process block 104. This difference mask is produced by detecting subject motion in each of a plurality of separate regions of the image frame 2. As illustrated in FIG. 9, the field of view (FOV) of each acquired image frame 2 is segmented into a plurality of regions (e.g. 7×7 pixel regions) and the changes in pixel values in each region are used to calculate a motion value for the corresponding region in a difference mask 103. In the preferred embodiment this motion value is calculated as the average of the absolute values of the differences in pixel values in the region, minus pixel values in the corresponding region of the previous image frame. For example, if substantial subject motion occurs in the region "X" of the recently acquired image frame 2, a corresponding high motion value is calculated and entered at the corresponding region "X" in the difference mask 103. On the other hand, if no motion is detected in the region "+" of the recently acquired image frame 2, a corresponding low motion value is produced and entered at the corresponding region "+" in the difference mask 103. Other methods may be employed to calculate a value indicative of subject motion in the region and the particular method chosen will depend on the particular clinical application.

Referring again to FIG. 7, after the difference mask 103 is produced a loop is entered in which a composite image is produced one region at a time. As indicated at decision block 106, the motion value in the difference mask 103 is examined to determine if motion in the region exceeds a threshold value. If not, that region in the composite image 3 is updated by accumulating the values from a large window of corresponding regions in the recently acquired image frames as indicated at process block 108. This is illustrated in FIG. 9 by arrows 109 where the region marked "+" is combined with the corresponding regions in previously acquired image frames 2 to update the region marked "+" in the composite image 3.

If motion is detected in the region being examined at decision block 106 on the other hand, the corresponding region in the composite image 3 is updated by replacing image data therein with image data from only the corresponding region in the current image frame 2 as indicated at process block 110. This is illustrated in FIG. 9 by an arrow 111, where the values in the image frame region marked "X" replaces the value in the corresponding region of the composite image 3. In either case, the updated region is added to the composite image 3, as indicated at process block 112 and the system loops back to examine the next region as indicated at process block 114. All of the regions in the difference mask 103 are examined in this manner and the corresponding regions in the composite image 3 are updated as determined at decision block 116. The time window over which image frame data is integrated to form the composite image 3 thus adapts to the subject motion detected in each region. The exact number of image frames accumulated for different motion conditions detected in a region will vary depending on the particular clinical application.

Referring still to FIG. 7, the updated composite image 3 is then used to perform HYPR image processing on the current image frame 2 as indicated at process block 118. As will be described below with respect to FIG. 8, the HYPR processing 118 is the same as that disclosed in the above-cited copending U.S. patent application Ser. No. 12/032,240 in which the higher SNR of the composite image 3 is transferred to the image frame 2. This enables the image frame 2 to be acquired at a much lower x-ray dose without losing significant quality. The HYPR processed image frame 2 is then displayed as indicated at process block 120 and the system loops back to acquire and process the next image frame. This procedure continues until the scan is completed as determined at decision block 122.

Regions in the composite image where no motion is detected continue to improve in quality as the corresponding regions in acquired image frames are accumulated. In this embodiment the accumulation is performed with a recursive filter that adds the current image frame region to a decay constant times the previous accumulated values in that region. In this embodiment, for example, the decay constant is set to 1.0, but this is expected to differ with other clinical applications. When motion is detected in the region that exceeds the threshold, the previous accumulated values are reset to zero so that the updated region in the composite image 3 has the same value as the pixel in the current image frame. Such "reset" composite regions will have a low SNR and it is preferable to filter it with a small blurring kernel to reduce noise. In some clinical applications it is preferable that the reset regions not be reset to zero. Instead, accumulation is performed over a preset shortened time window such as 2 to 4 image frames.

There are many alternative ways to update each region in the composite image 3 as a function of detected motion in the region. For example, multiple motion thresholds may be established and the update procedure may differ for each. The difference may be in the number of past image frames that are accumulated (i.e., the length of the time window) or in the value of the decay constant that is used. A motion history of each region may also be maintained and this additional information may be used to vary the update procedure. Thus, even though a motion threshold is not exceeded during any single image frame acquisition, the accumulation of motion over the last number of acquired image frames may exceed an "accumulated motion" threshold. This may result in the shortening of the accumulation time window for the current image frame.

Figure 8:
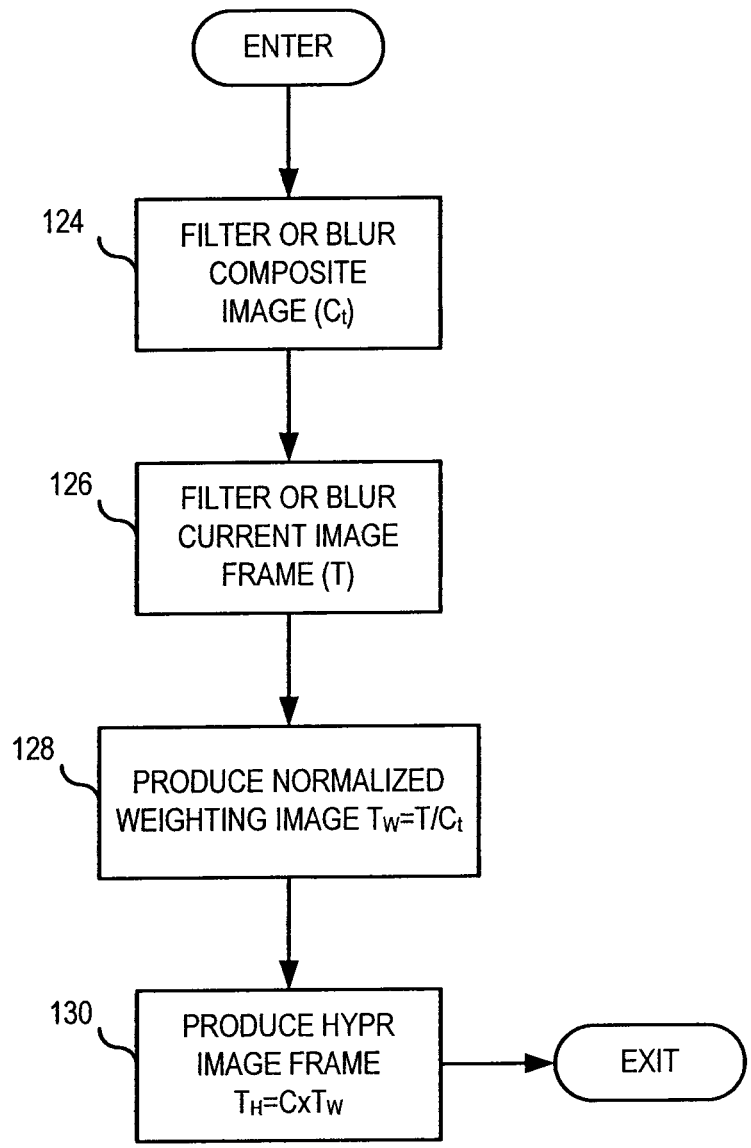
FIG. 8 is a flow chart of the HYPR processing used in the process of FIG. 7.

As shown in FIG. 8, the HYPR process used in this embodiment is very similar to that described above and illustrated in FIG. 17. The first step is to produce a normalized weighting image using the current 2D radiograph image frame 2 and the updated composite image 3. More specifically, the updated composite image 3 is "blurred" by filtering as indicated at process block 124. The filtering is a convolution process in which the updated 2D composite image array 3 is convolved with a filter kernel. In the preferred embodiment the filter kernel is a 7×7 square filter kernel. The kernel size should be selected so that when the blurring is done the kernel does not include much information from outside the subject of interest (for example a blood vessel). The filter kernel should be on the order of the dimension of the objects being examined or somewhat smaller. Gaussian or other smooth filter kernels may also be used and the resulting filter function being performed is essentially low pass filtering.

Referring still to FIG. 8, the current 2D image frame 2 is also blurred or filtered in the same manner as indicated at process block 126. That is, the 2D radiograph image frame array 2 is convolved with the filter kernel to perform a low pass filtering function. As indicated at process block 128, the normalized weighting image ($T_W$) is then produced by dividing pixel values in the filtered current image frame (T) by the corresponding pixel values in the filtered composite image ($C_t$).

As indicated at process block 130, a highly constrained (HYPR) image frame 4 is then produced. This image frame 4 is produced by multiplying the updated composite image array 3 by the normalized weighting image array ($T_W$). This is a multiplication of corresponding pixel values in the two images. The resulting 2D HYPR image is then output to the display 52 as described above.

It should be apparent to those skilled in the art that this same method can be performed to reconstruct 3D images. The steps are the same, but they are carried out on 3D volumes.

Figure 10:
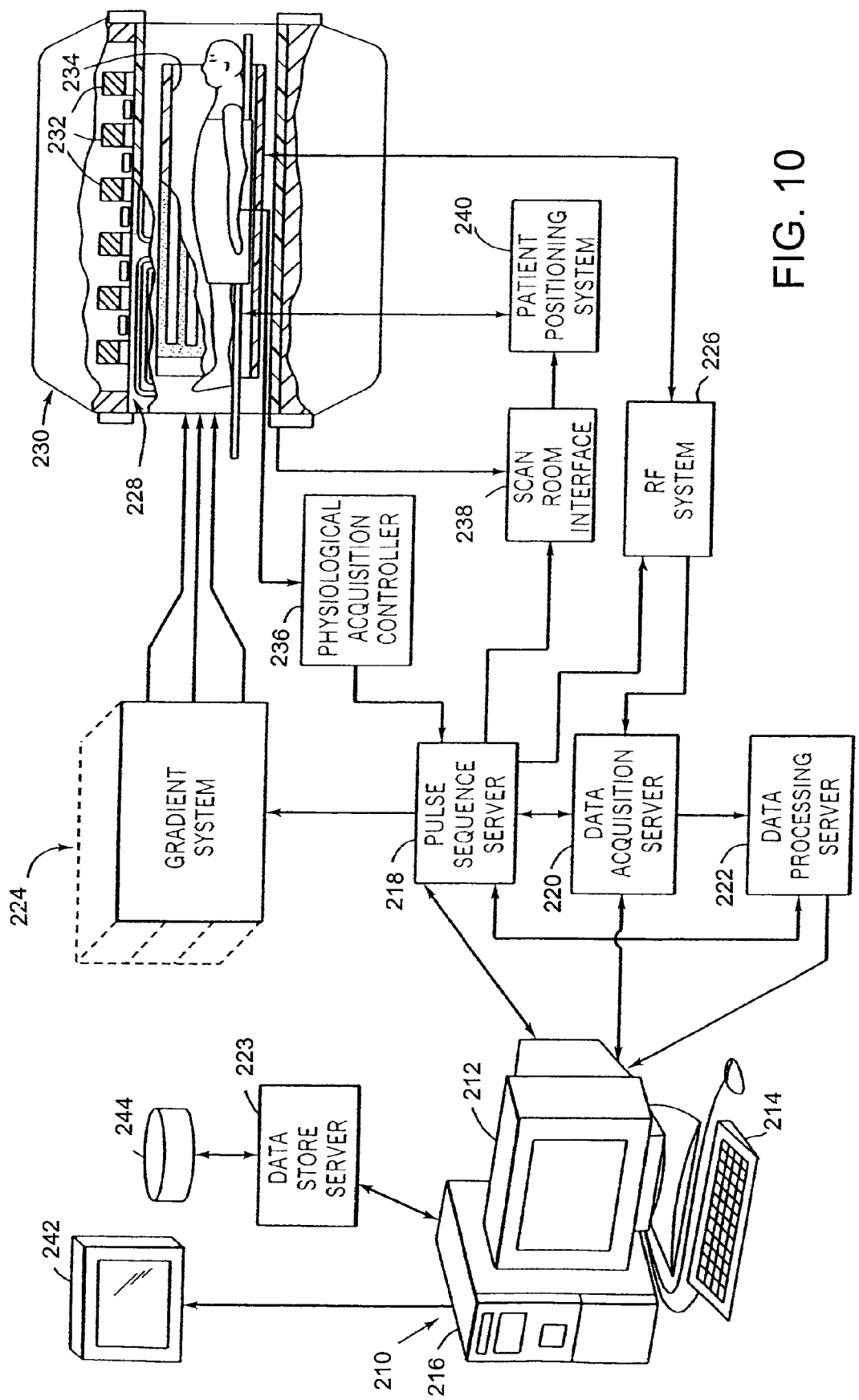
FIG. 10 is a block diagram of an MRI system which employs a second preferred embodiment of the invention.

Another embodiment of the invention is applied to cardiac imaging using a magnetic resonance imaging (MRI) system shown in FIG. 10. As with the previous embodiment described above, this embodiment forms a composite image to employ HYPR processing by examining subject motion on a region-by-region basis. The MRI system includes a workstation 210 having a display 212 and a keyboard 214. The workstation 210 includes a processor 216 which is a commercially available programmable machine running a commercially available operating system. The workstation 210 provides the operator interface which enables scan prescriptions to be entered into the MRI system.

The workstation 210 is coupled to four servers: a pulse sequence server 218; a data acquisition server 220; a data processing server 222, and a data store server 223. In the preferred embodiment the data store server 223 is performed by the workstation processor 216 and associated disc drive interface circuitry. The remaining three servers 218, 220 and 222 are performed by separate processors mounted in a single enclosure and interconnected using a 64-bit backplane bus. The pulse sequence server 218 employs a commercially available microprocessor and a commercially available quad communication controller. The data acquisition server 220 and data processing server 222 both employ the same commercially available microprocessor and the data processing server 222 further includes one or more array processors based on commercially available parallel vector processors.

The workstation 210 and each processor for the servers 218, 220 and 222 are connected to a serial communications network. This serial network conveys data that is downloaded to the servers 218, 220 and 222 from the workstation 210 and it conveys tag data that is communicated between the servers and between the workstation and the servers. In addition, a high speed data link is provided between the data processing server 222 and the workstation 210 in order to convey image data to the data store server 223.

The pulse sequence server 218 functions in response to program elements downloaded from the workstation 210 to operate a gradient system 224 and an RF system 226. Gradient waveforms necessary to perform the prescribed scan are produced and applied to the gradient system 224 which excites gradient coils in an assembly 228 to produce the magnetic field gradients $G_x$, $G_y$, and $G_z$ used for position encoding NMR signals. The gradient coil assembly 228 forms part of a magnet assembly 230 which includes a polarizing magnet 232 and a whole-body RF coil 234.

RF excitation waveforms are applied to the RF coil 234 by the RF system 226 to perform the prescribed magnetic resonance pulse sequence. Responsive NMR signals detected by the RF coil 234 are received by the RF system 226, amplified, demodulated, filtered and digitized under direction of commands produced by the pulse sequence server 218. The RF system 226 includes an RF transmitter for producing a wide variety of RF pulses used in MR pulse sequences. The RF transmitter is responsive to the scan prescription and direction from the pulse sequence server 218 to produce RF pulses of the desired frequency, phase and pulse amplitude waveform. The generated RF pulses may be applied to the whole body RF coil 234 or to one or more local coils or coil arrays.

The RF system 226 also includes one or more RF receiver channels which may be connected to a corresponding plurality of local coils or to a corresponding plurality of coil elements in a coil array. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2-Q^2},$$

and the phase of the received NMR signal may also be determined:

$$\phi=\tan^{-1} Q/I.$$

The pulse sequence server 218 also optionally receives patient data from a physiological acquisition controller 236. The controller 236 receives signals from a number of different sensors connected to the patient, such as ECG signals from electrodes or respiratory signals from a bellows. Such signals are typically used by the pulse sequence server 218 to synchronize, or "gate", the performance of the scan with the subject's respiration or heart beat.

The pulse sequence server 218 also connects to a scan room interface circuit 238 which receives signals from various sensors associated with the condition of the patient and the magnet system. It is also through the scan room interface circuit 238 that a patient positioning system 240 receives commands to move the patient to desired positions during the scan.

It should be apparent that the pulse sequence server 218 performs real-time control of MRI system elements during a scan. As a result, it is necessary that its hardware elements be operated with program instructions that are executed in a timely manner by run-time programs. The description components for a scan prescription are downloaded from the workstation 210 in the form of objects. The pulse sequence server 218 contains programs which receive these objects and converts them to objects that are employed by the run-time programs.

The digitized NMR signal samples produced by the RF system 226 are received by the data acquisition server 220. The data acquisition server 220 operates in response to description components downloaded from the workstation 210 to receive the real-time NMR data and provide buffer storage such that no data is lost by data overrun. In some scans the data acquisition server 220 does little more than pass the acquired NMR data to the data processor server 222. However, in scans which require information derived from acquired NMR data to control the further performance of the scan, the data acquisition server 220 is programmed to produce such information and convey it to the pulse sequence server 218. For example, during prescans NMR data is acquired and used to calibrate the pulse sequence performed by the pulse sequence server 218. Also, navigator signals may be acquired during a scan and used to adjust RF or gradient system operating parameters or to control the view order in which k-space is sampled. And, the data acquisition server 220 may be employed to process NMR signals used to detect the arrival of contrast agent in an MRA scan. In all these examples the data acquisition server 220 acquires NMR data and processes it in real-time to produce information which is used to control the scan.

The data processing server 222 receives NMR data from the data acquisition server 220 and processes it in accordance with description components downloaded from the workstation 210. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 222 are conveyed back to the workstation 210 where they are stored. Real-time images are stored in a data base memory cache (not shown) from which they may be output to operator display 212 or a display which is located near the magnet assembly 230 for use by attending physicians. Batch mode images or selected real time images are stored in a host database on disc storage 244. When such images have been reconstructed and transferred to storage, the data processing server 222 notifies the data store server 223 on the workstation 210. The workstation 210 may be used by an operator to archive the images, produce films, or send the images via a network to other facilities.

Figure 11:
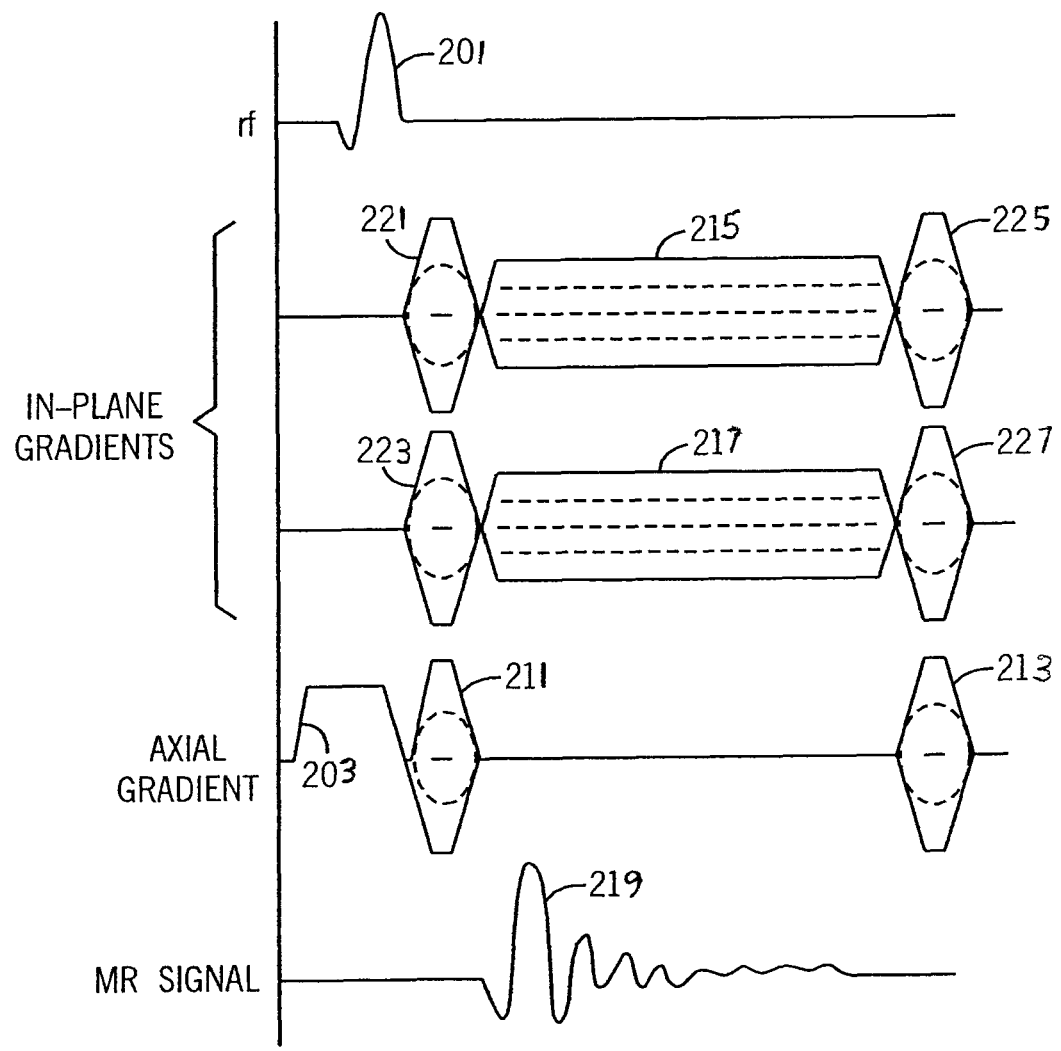
FIG. 11 is a graphic representation of a pulse sequence employed in the MRI system of FIG. 10.

To practice this embodiment of the invention NMR data is acquired using a projection reconstruction, or radial, pulse sequence shown in FIG. 11. This is a fast gradient-recalled echo pulse sequence in which a selective, asymmetrically truncated sinc rf excitation pulse 201 is produced in the presence of a slice-select gradient 203. The flip angle of the rf pulse 201 is set near the Ernst angle for $T_1$ shortened blood which is typically 30° to 40°.

Figure 12:
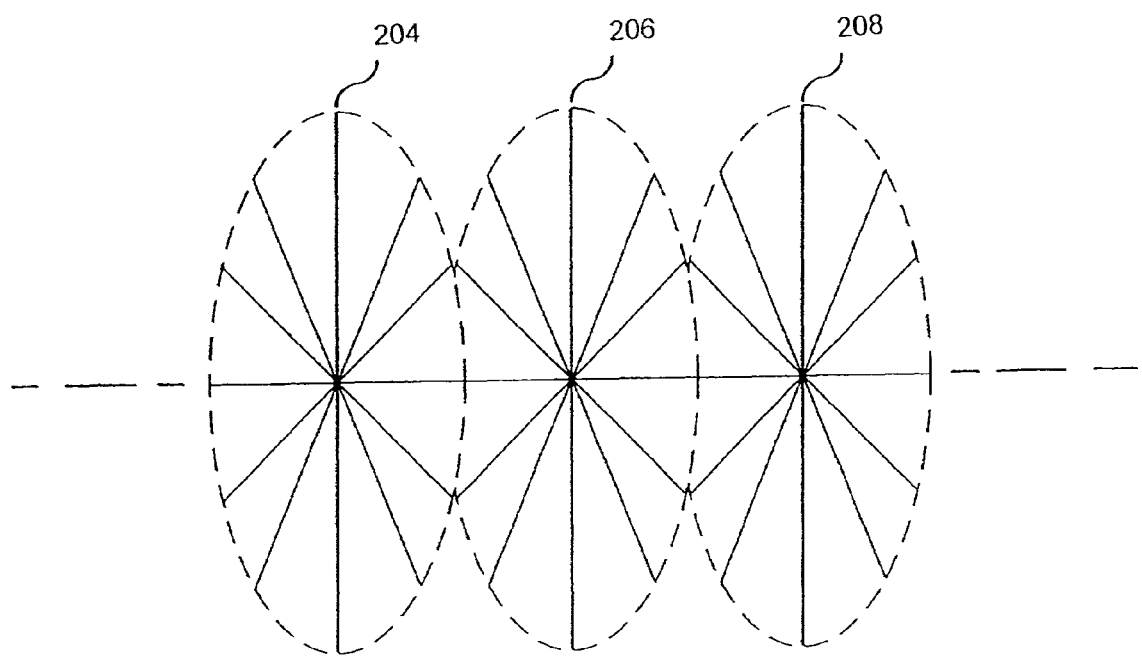
FIG. 12 is a pictorial representation of the k-space sampling performed by the pulse sequence of FIG. 11.

This pulse sequence may be used to acquire a single 2D slice by sampling in a single k-space circular plane, but in the preferred embodiment a plurality of circular k-space planes are sampled as shown at 204, 206 and 208 in FIG. 12. When multiple 2D slices are acquired the axial gradient 203 is a slab select gradient followed by a phase encoding gradient lobe 211 and a rewinder gradient lobe 213 of opposite polarity. This axial phase encoding gradient 211 is stepped through values during the scan to sample from each of the 2D k-space planes 204, 206 and 208.

Two in-plane readout gradients 215 and 217 are played out during the acquisition of an NMR echo signal 219 to sample k-space in a 2D plane 204, 206 or 208 along a radial trajectory. These in-plane gradients 215 and 217 are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe 221 and 223 and followed by a rewinder gradient lobe 225 and 227.

It should be apparent to those skilled in the art that sampling trajectories other than the preferred straight line trajectory extending from one point on the k-space peripheral boundary, through the center of k-space to an opposite point on the k-space peripheral boundary may be used. One variation is to acquire a partial NMR echo signal 219 which samples along a trajectory that does not extend across the entire extent of the sampled k-space volume. Another variation which is equivalent to the straight line projection reconstruction pulse sequence is to sample along a curved path rather than a straight line. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. It should also be apparent that the present invention may be employed with 3D as well as 2D versions of these sampling methods and references to the term "pixel" as used hereinafter is intended to refer to a location in either a 2D or a 3D image.

Figure 13:
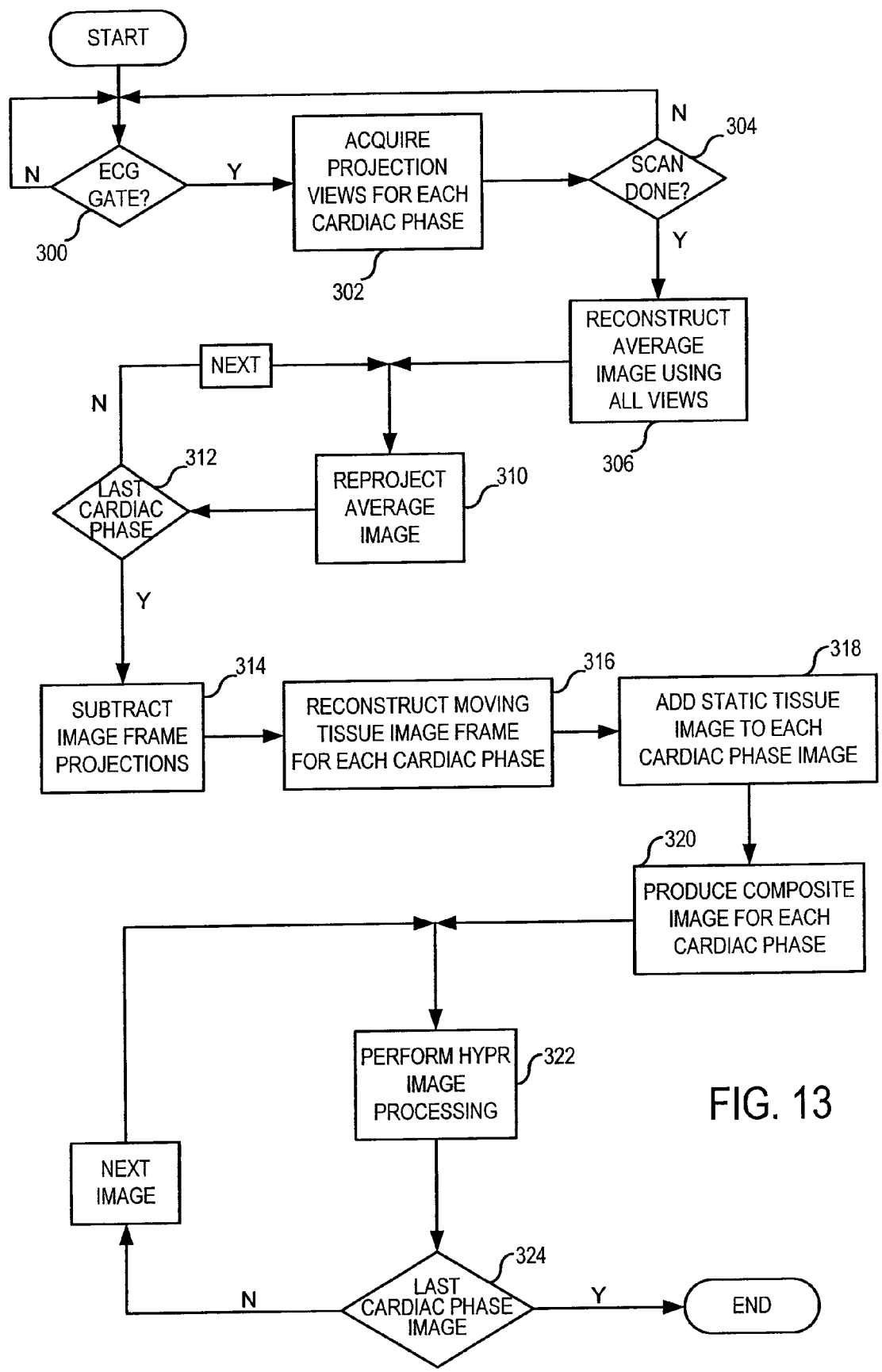
FIG. 13 is a flow chart showing a cardiac imaging method using the MRI system of FIG. 10.
Figure 14:
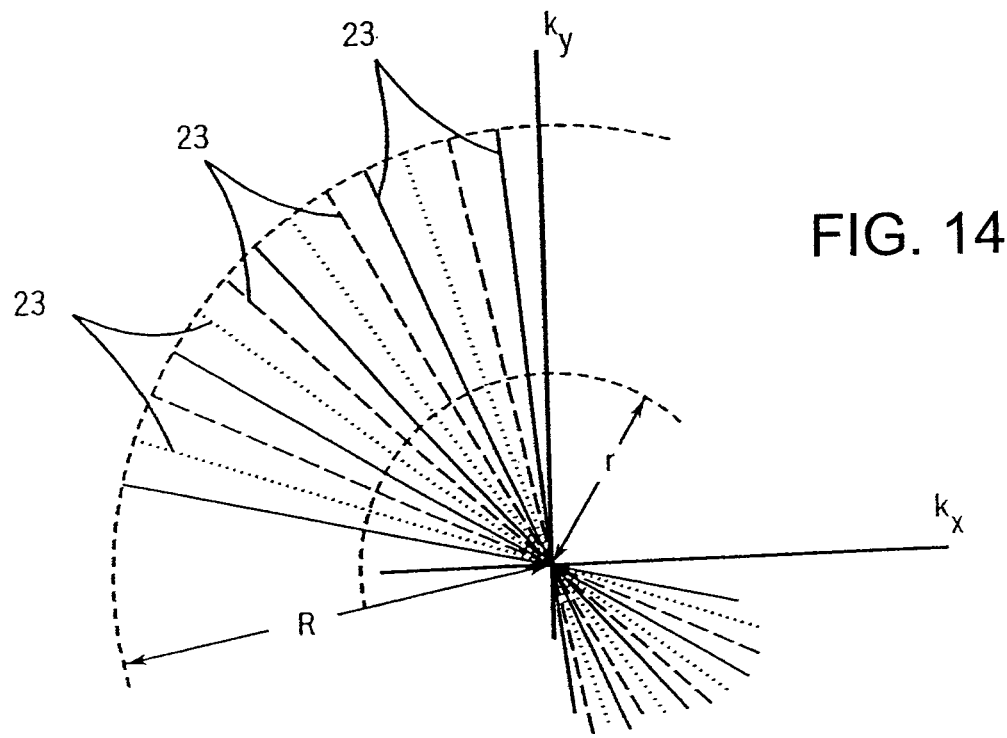
FIG. 14 is a graphic representation of the interleaved projections acquired with the MRI system to practice the method of FIG. 13.

Referring particularly to FIG. 13, a series of cardiac gated image frames are acquired that depict the heart at a corresponding number of different cardiac phases. As indicated at decision block 300, the system waits for an ECG gating signal and when the signal is received the pulse sequence of FIG. 11 is performed to acquire projection views of the moving heart and surrounding stationary tissues from each of a plurality (e.g., N=20) cardiac phases as indicated at process block 302. Three 2D slices are effectively acquired at each cardiac phase using this particular pulse sequence, and the projection views are interleaved and equally spaced as shown in FIG. 14, where the dotted lines 231 indicate the k-space sampling trajectories acquired for one slice, dashed lines 233 indicate the k-space sampling trajectories acquired for a second slice and solid lines 235 indicate the k-space sampling pattern for the third slice. The acquisition continues until the prescribed number of projection views (e.g., n=30) are acquired for each of the three 2D slices at each cardiac phase as detected at decision block 304. N=20 image frames are thus acquired with n=30 interleaved projection views in each 2D slice image frame. Not only are the projection views acquired at each cardiac phase interleaved for each slice as described above, but they are also interleaved with the projection views acquired at the other cardiac phases.

There are many different ways to produce a list of projection view angles φ during the scan that will interleave all the acquired views. The view angles φ will depend on such factors as the number of cardiac phases (N) to be acquired during each heartbeat, the number of projection views to be acquired for each cardiac phase during one heart beat ($n_{pr}$), and the number of heart beats (H) during the scan. The formula used in the preferred embodiment to calculate the view angle for the $n^{th}$ cardiac phase in the $k^{th}$ heartbeat is:

$$\phi = \Delta_1 \times K + \Delta_2 \times B(n) + [0:180/n_{pr}:180]$$

where:
$\Delta_1 = 180/(H \times n_{pr})$
$\Delta_2 = 180/(H \times N \times n_{pr})$
B(n)=bit reversal algorithm for generating pseudo random permutation of a sequence of integers. The view angles φ for each of the slices are also interleaved, and this is achieved by incrementing the starting angle in each slice by 180°/number of slices.

Referring still to FIG. 13, an image is reconstructed using all the acquired projection views (n×N) for each slice location as indicated at process block 306. This is a conventional reconstruction process in which the acquired NMR signals are first Fourier transformed along the axial gradient direction to produce projections at the three slice locations along that axis. The radial k-space sample points for each 2D slice are then regridded to a Cartesian grid and then a two-dimensional Fourier transformation is performed. The resulting average image will depict the heart as a blur due to its motion, but because all of the acquired, interleaved projection views at each slice in each cardiac phase are used in the reconstruction, the surrounding static structures will be depicted accurately and with few artifacts.

Figure 16:
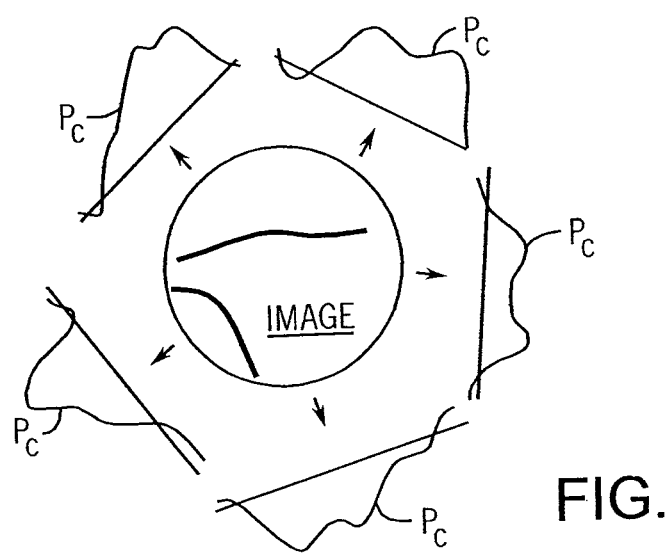
FIG. 16 is a pictorial representation of a reprojection step in the method of FIG. 13.

As indicated at process block 310, the resulting average image is then reprojected at all the projection view angles for one of the N cardiac phases. This is illustrated in FIG. 16 and is accomplished with a conventional Radon transformation as described, for example, in "Computed Tomography Principles, Design, Artifacts and Recent Advances", Jiang Hsieh, SPIE Press 2003, Chapter 3. A projection contour is thus produced at each view angle acquired for each slice at this cardiac phase. The reprojection step 310 is repeated for each cardiac phase, and when the last cardiac phase projection has been reprojected as detected at decision block 312, a set of average image frame reprojections have been produced.

As indicted at process block 314, the next step is to subtract each of the average image reprojections from the corresponding originally acquired projections. This results in a set of n=30 projection views for each 2D slice in each of the acquired N=20 cardiac phases which depict only the moving tissues. In other words, the signals from the static tissues are subtracted out and the remaining signals are essentially high pass filtered moving tissue signals.

As indicated at process block 316, the next step is to reconstruct moving tissue images from the moving tissue reprojections. This is done for each slice and at each cardiac phase. The reconstruction is preferably a conventional image reconstruction as described above at process block 306, however a HYPR reconstruction can also be performed as described in the above-cited copending U.S. patent application entitled "Reconstruction Method For Images of the Beating Heart", which is incorporated herein by reference. As indicated at process block 318, the static tissue image is then combined with the moving tissue images to form three image frames for each cardiac phase. This is accomplished by adding the values at corresponding pixels in the images. This adds the good static tissue signals and it adds back the low frequency moving tissue signals previously subtracted out in process block 314.

Referring still to FIG. 13, a composite image is calculated next as indicated at process block 320. As will be described in detail below, a composite image is produced for each cardiac phase and these are used in the HYPR processing of the image frames at each cardiac phase. More specifically, a loop is entered in which each image frame is HYPR processed as indicated at process block 322. This processing enhances the image frames produced above by transferring the higher SNR of the composite image to the processed image frame. In addition, it reduces under sampling and motion artifacts. Each image frame is processed in this manner until all of the cardiac phase image frames have been processed as determined at decision block 324. This HYPR processing is the same method as that described above for process block 118 which is shown in FIG. 7 with the steps shown in FIG. 8.

The results achieved with this embodiment result from the quality composite image produced for each cardiac phase at process block 320. For each cardiac phase the composite begins with the image frame for that cardiac phase and accumulates, or integrates, the image values from other cardiac phase image frames. As with the embodiment described above, this accumulation is done on a region-by-region basis such that regions with little motion will accumulate to produce a higher quality composite than regions with greater motion.

Figure 15:
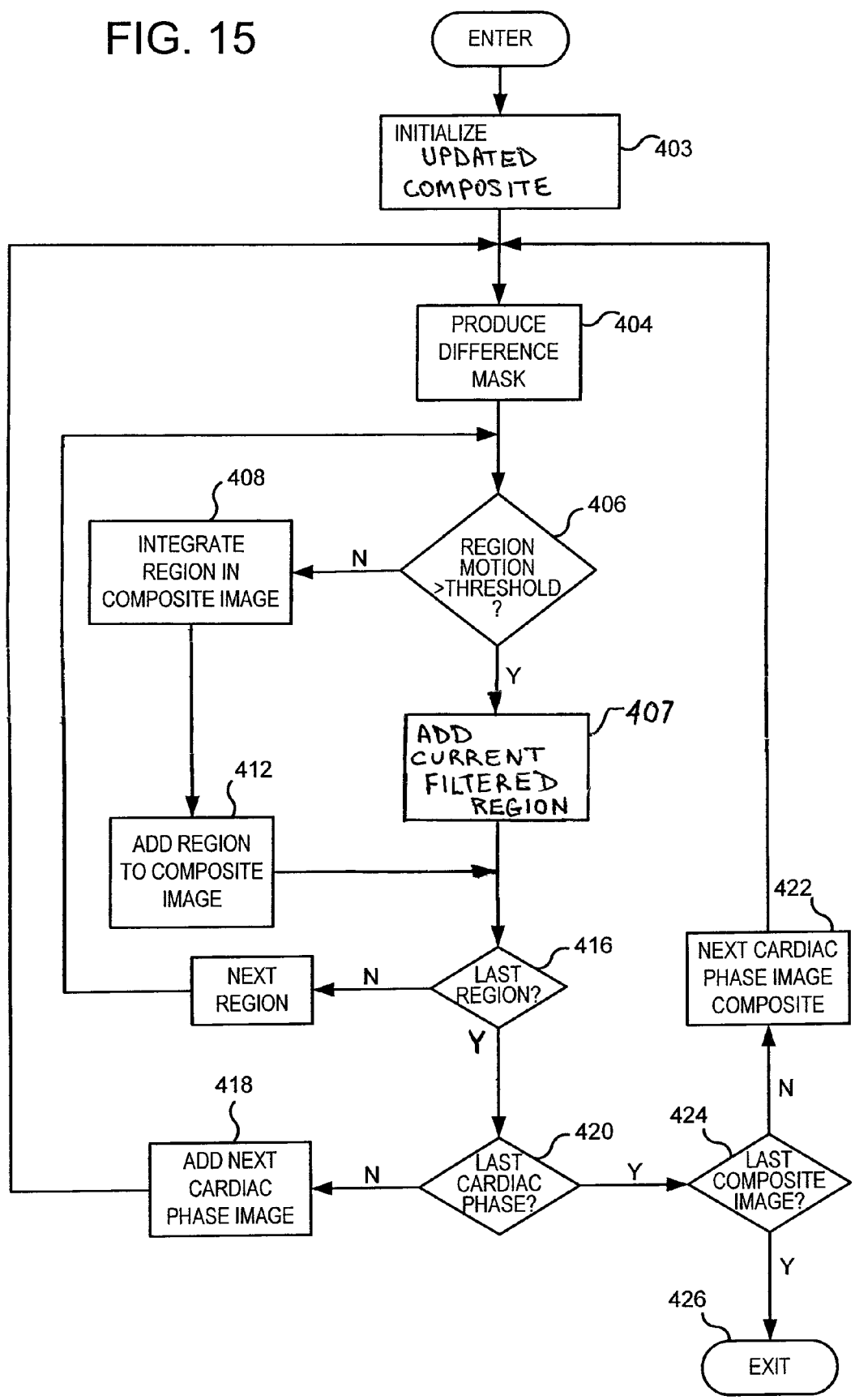
FIG. 15 is a flow chart of the steps used to produce composite images in the method of FIG. 13.

Referring particularly to FIG. 15, the first step in the production of a composite image is to initialize an updated composite image for the current cardiac phase as indicated at process block 403. A loop is then entered in which each of the other cardiac phase images acquired during the scan are examined, region by region, to determine which regions therein can be accumulated with the values for the current cardiac phase image. For each candidate cardiac phase image the first step is to produce a difference mask as indicated at process block 404. This can be done in a number of ways, but in this embodiment a value is calculated for each 7 pixel by 7 pixel region which is the difference between the average values of the pixels in the current cardiac phase image frame region and the average value of the corresponding pixels in the candidate cardiac phase image. A further loop is then entered in which each region is examined by thresholding this difference mask value. As indicated at decision block 406, if a region in a candidate cardiac image frame has excessive motion as evidenced by the corresponding region of the difference mask, that region is not accumulated. Instead, the current cardiac phase image frame region is added to the composite image after blurring, or low pass filtering the region to reduce noise as indicated at process block 407. Otherwise, the pixel values in the region of the candidate cardiac phase image frame being considered are accumulated with the current composite image pixel values in the corresponding region as indicated at process block 408. The integrated pixel values for this region are then added to the updated composite image values as indicated at process block 412.

The composite image for the current cardiac phase is selectively accumulated in this manner until each region of the difference mask is processed as determined at decision block 416. As a result, the regions of a candidate cardiac phase image in which little motion has occurred will be integrated to improve composite image quality. On the other hand, regions where substantial motion has occurred relative to the current cardiac phase image frame are not accumulated and do not blur the resulting composite image.

This region-by-region composite image integration process is applied to each of the candidate cardiac phase images acquired during the scan as indicated at process block 418. When the last acquired cardiac phase image has been integrated as determined at decision block 420, the updated composite image for the current cardiac phase is completed. This process is repeated as indicated at process block 422 to produce a composite image for each slice at each cardiac phase. When all composites have been produced as determined at decision block 424, the process exits at 426 and the HYPR processing proceeds as described above.

In the above embodiments of the invention the detection of subject motion is done on a frame-by-frame basis, a region-by-region basis or a pixel-by-pixel basis. The composite image is then produced by accumulating data from prior image frames with the current image frame on a frame-by-frame, region-by-region or pixel-by-pixel basis as a function of the detected subject motion.

In the following embodiments the composite image is also produced in such a manner that subject motion is taken into account. However, rather than characterizing the formation of the composite as adaptively accumulating data from prior image frames, the formation of the composite may be characterized as adaptively updating the existing composite image by registering the spatial location of the existing composite image data before combining it with data from the current image frame. As with the methods described above, this adaptive updating of the composite image can be done on a frame-by-frame, region-by-region or pixel-by-pixel basis.

Figure 21:
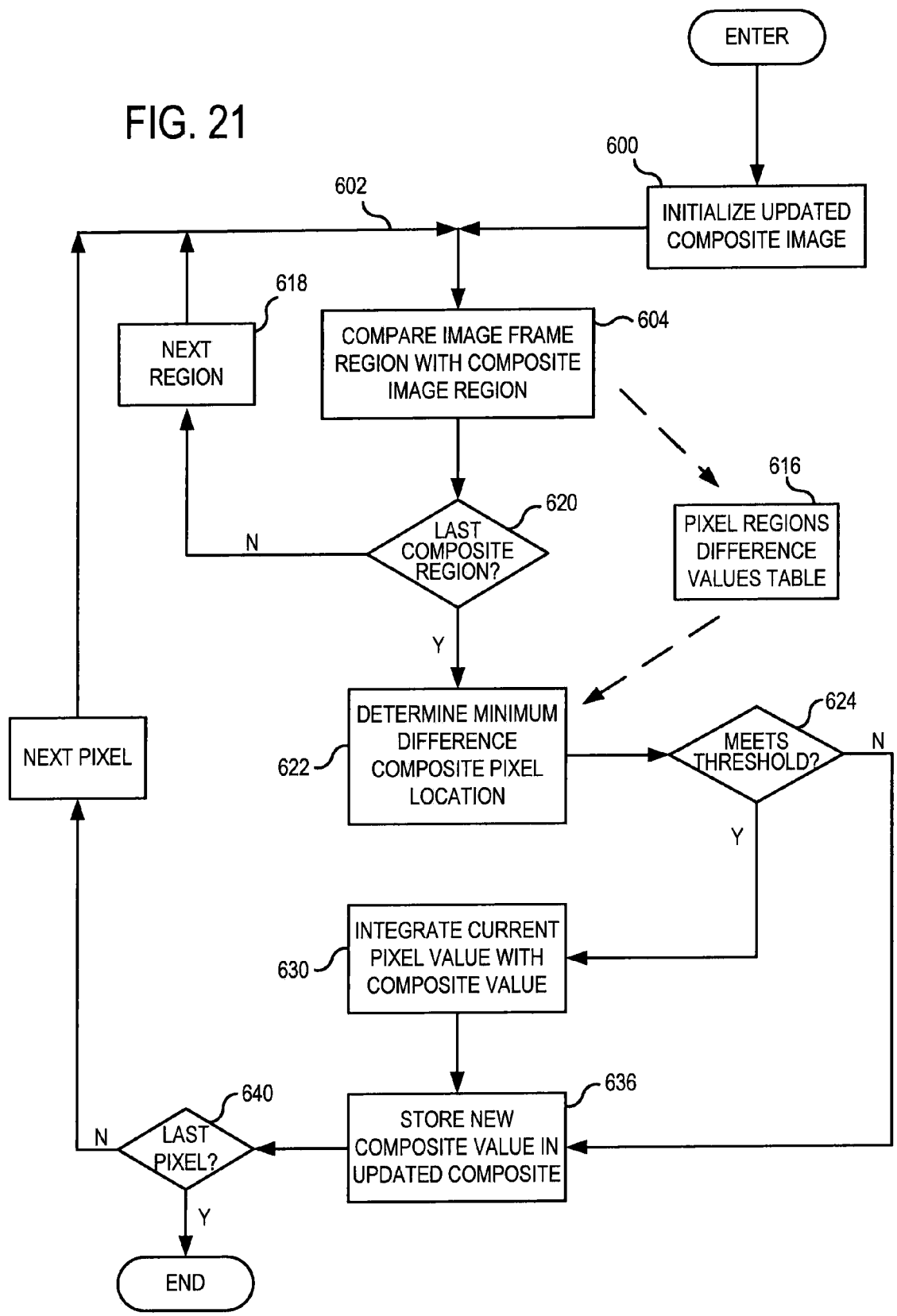
FIG. 21 is a flow chart showing the steps performed in another embodiment of the invention.

Referring particularly to FIG. 21, the preferred method for updating a composite image using the registration technique is performed on a pixel-by-pixel basis. As indicated at process block 600 an updated composite image data structure is initialized and then a loop is entered at 602 in which the value of each pixel in the updated composite image is calculated. This is done by searching in the current composite image for the location of the current image frame pixel being processed. This is done by comparing the values of a region of pixels surrounding each pixel. Referring particularly to FIG. 22, for example, a pixel 606 has a spatial location (x, y) in the current image frame 608, and if there is no subject motion, the same pixel value will be found at the same spatial location (x, y) 606 in the current composite image 610. When motion occurs, however, the pixel value locations will be different and the objective is to locate the current image frame pixel in the current composite image 610. As indicated by arrow 612, this is done by searching in a pattern around the corresponding pixel location 606 in the composite image 610. The size and shape of this search pattern will depend on the particular medical application.

Referring still to FIGS. 21 and 22, this search is conducted by comparing the pixel values in a region 614 surrounding the current image frame pixel 606 with the values in a similar displaced region 615 in the current composite image 610 as indicated at process block 604. In the preferred embodiment this comparison is performed by summing the absolute differences between corresponding pixel values in the two regions 614 and 615 and storing the resulting "regions difference value" in a data table 616. The regions 614 and 615 are each 5×5 pixels in the preferred embodiment although other sizes may also be used. This comparison step 604 is repeated as indicated by process block 618, as the region 615 is moved around the current composite image 610 in the prescribed search pattern 612 until the search pattern is completed, as indicated at decision block 620. The size of the search pattern 612 will depend on the amount of anticipated subject motion from frame-to-frame, which in turn will depend on the particular application. At this juncture the table 616 stores the results of all the candidate pixel location comparisons, and as indicated at process block 622, the location of the desired pixel value in the composite image 610 is determined next by identifying the displacement of region 615 that yielded the minimum regions difference value. As indicated at decision block 624, this minimum regions difference value is then compared with a difference threshold value. In the preferred embodiment this minimum threshold value is set to 20% of the integral of pixel values in the current image frame region 614. If the minimum regions difference value is greater than this minimum threshold value, the current image frame pixel value 606 is transferred to the corresponding pixel location 606 in the updated composite image 626 as indicated by dotted line 628. This will be the case when there is significant motion in the region of pixel 606. As indicated at process block 630, however, in most cases the location of the current image frame pixel 606 will be found in the current composite image 610 and the two values will be integrated together as shown at summation 632 in FIG. 22 and stored at pixel location 606 in the updated composite image 626 as indicated by process block 636 in FIG. 21 and shown by dashed line 634 in FIG. 22. The integration is performed by adding the current image frame pixel value to the product of the decay constant times the current composite image pixel value and dividing the result by the number of previous contributions to the composite pixel value plus one.

Referring particularly to FIG. 21, the above process is repeated until each pixel location in the current image frame 608 is examined and the value of the corresponding pixel location in the updated composite image 626 is calculated as indicated at decision block 640. The updated composite image is then ready for use in the HYPR processing of the current image frame as described above.

In the above preferred embodiment each pixel in the current image frame is registered with a corresponding pixel in the current composite image in order to update a pixel in the updated composite image. This same registration process can also be performed to update the composite image one region at a time. For example, the entire 5 pixel×5 pixel region may be updated after examining the current composite image around the corresponding region location in a prescribed search pattern. In this case the search will yield a displacement vector that is used to shift the location of all pixels in the region. This will, of course, shorten the time needed to update the composite image, but in doing this, spatial resolution of the subject motion is lost. It is expected that the size of the region to be updated will be set by an operator anywhere from one pixel to the entire image frame depending on the particular application. When the prescribed updated region is small (e.g., one pixel as described above) the prescribed size of the surrounding region to be used in the registration search pattern will be set to a size on the order of the expected local motion during one image frame interval, whereas when the prescribed updated region is large (e.g., the entire image), the prescribed size of the region to be used in the registration search pattern will be chosen to correspond to the amount of bulk subject motion expected from one frame to the next.

The invention claimed is:

1. A non-transitory computer readable storage medium comprising instructions stored thereon that, when executed by a processor, cause the processor to carry out steps for producing an updated composite image of a subject for use in highly-constrained projection (HYPR) processing an acquired current image frame, the instructions causing the processor to carry out the steps of:
    a) dividing the current image frame into a plurality of spatial regions based on a location of the spatial region in the current image frame;
    b) determining subject motion in each of the spatial regions; and
    c) producing the updated composite image on a region-by-region basis by combining data in each current image frame region with other acquired image frame data in a manner determined by the subject motion detected in that region;
    wherein step c) includes multiplying the updated composite image by a decay constant and adding the data in the current image frame to the result of the multiplying step.

2. The non-transitory computer readable storage medium as recited in claim 1 in which each region has a size of one image frame pixel.

3. The non-transitory computer readable storage medium as recited in claim 1 in which step b) is performed by acquiring a signal from the subject which indicates cardiac phase and subject motion is implied from this signal as the current image frame is acquired.

4. The non-transitory computer readable storage medium as recited in claim 1 in which the decay constant ranges in value up to 1.0.

5. The non-transitory computer readable storage medium as recited in claim 1 in which a current composite image is formed from said other acquired image frame data, and a registration and integration are performed between the current composite image and the current image frame to form the updated composite image, the registration being performed separately for each region.

6. The non-transitory computer readable storage medium as recited in claim 5 in which the regions are each one image frame pixel in size.

7. The non-transitory computer readable storage medium as recited in claim 5 in which the registration includes searching for a region of data in the current composite image that best matches the data in a region of the current image frame.

8. The non-transitory computer readable storage medium as recited in claim 7 in which the registration includes shifting the location of a region of data in the current composite image.

9. The non-transitory computer readable storage medium as recited in claim 5, in which the integration also includes dividing the result of the multiplying step by a number indicative of the number of the other image frames used to form the current composite image.

10. The non-transitory computer readable storage medium as recited in claim 1 in which the updated composite image is formed by accumulating the other acquired image frame data over a time window that includes the acquisition of the current image frame, and the duration of the time window is determined separately for each region of the current image frame such that the amount of image frame data accumulated for each region is determined by subject motion within the region.

11. The non-transitory computer readable storage medium as recited in claim 10 in which the regions are each one image frame pixel in size.

12. A non-transitory computer readable storage medium comprising instructions stored thereon that, when executed by a processor, cause the processor to carry out steps for producing an updated composite image from a current composite image formed from acquired image frames for use in highly-constrained projection (HYPR) processing a current image frame, the instructions causing the processor to carry out the steps of:
    a) spatially registering the current composite image with the current image frame;
    b) integrating data in the current image frame with registered data in the current composite image; and
    c) storing the integrated data in the updated composite image at locations corresponding to the locations of the integrated current image frame data;
    wherein step b) includes multiplying the updated composite image by a decay constant and adding the data in the current image frame to the result of the multiplying step.

13. The non-transitory computer readable storage medium as recited in claim 12 in which step a) is performed on a pixel-by-pixel basis.

14. The non-transitory computer readable storage medium as recited in claim 12 in which step a) includes:
- a)i) detecting subject motion; and
- a)ii) shifting the location of the current composite image to offset the detected motion.

15. The non-transitory computer readable storage medium as recited in claim 12 in which step b) includes setting the registered data in the current composite image to zero when optimal registration is not achieved.

16. The non-transitory computer readable storage medium as recited in claim 12 in which steps b) and c) are performed on separate regions within the current image frame.

17. The non-transitory computer readable storage medium as recited in claim 12 in which steps b) and c) are performed on separate pixels within the current image frame.

18. The non-transitory computer readable storage medium as recited in claim 12 in which the current image frame is divided into regions and step a) is performed for each region.

19. The non-transitory computer readable storage medium as recited in claim 18 in which step a) includes:
- searching for a region of data in the current composite image that best matches the data in a region of the current image frame.

20. The non-transitory computer readable storage medium as recited in claim 19 in which the best match is determined by:
- a)i) calculating the sum of the differences in pixel values of the region of the current image frame and the pixel values in a plurality of regions in the current composite image; and
- a)ii) selecting the region in the current composite image that results in the lowest sum.

21. The non-transitory computer readable storage medium as recited in claim 12 in which step a) includes locating in the current composite image the pixel value that corresponds to each pixel value in the current image frame.

22. The non-transitory computer readable storage medium as recited in claim 21 in which the location of each pixel value in the current composite image is determined by:
- a)i) calculating the sum of the differences in pixel values of a region around the pixel in the current image frame and the pixel values in regions surrounding a plurality of pixel locations in the current composite image; and
- a)ii) selecting the pixel value at the pixel location that produces the minimum sum.

23. The non-transitory computer readable storage medium as recited in claim 12 in which step b) includes:
- b)i) multiplying the registered data in the current composite image by a decay constant that ranges in value up to 1.0; and
- b)ii) adding the data in the current image frame to the result produced in step b)i).

24. The non-transitory computer readable storage medium as recited in claim 23 which step b) also includes:
- b)iii) dividing the result produced in step b)ii) by a number indicative of the number of integrated image frames.

\* \* \* \* \*